US010696602B2

(12) United States Patent
Knochenmus et al.

(10) Patent No.: US 10,696,602 B2
(45) Date of Patent: Jun. 30, 2020

(54) ORGANICALLY CHELATED MINERAL COMPOSITIONS AND METHODS THEREOF

(71) Applicant: Ralco Nutrition, Inc., Marshall, MN (US)

(72) Inventors: Brian Jon Knochenmus, Lynd, MN (US); Jon Kent Knochenmus, Lynd, MN (US); Richard Dale Lamb, Balaton, MN (US); Myrra Arlene Lamb, Balaton, MN (US)

(73) Assignee: Ralco Nutrition, Inc., Marshall, MN (US)

( * ) Notice: Subject to any disclaimer, the term of this patent is extended or adjusted under 35 U.S.C. 154(b) by 0 days.

(21) Appl. No.: 14/043,083

(22) Filed: Oct. 1, 2013

(65) Prior Publication Data

US 2014/0026629 A1 Jan. 30, 2014

Related U.S. Application Data

(62) Division of application No. 12/835,545, filed on Jul. 13, 2010, now Pat. No. 8,575,212.

(60) Provisional application No. 61/289,295, filed on Dec. 22, 2009.

(51) Int. Cl.
*C05F 11/00* (2006.01)
*C07F 15/06* (2006.01)
*A23K 20/20* (2016.01)
*A23K 20/105* (2016.01)
*C05D 9/00* (2006.01)

(52) U.S. Cl.
CPC ............ *C05F 11/00* (2013.01); *A23K 20/105* (2016.05); *A23K 20/20* (2016.05); *A23K 20/30* (2016.05); *C05D 9/00* (2013.01); *C07F 15/065* (2013.01)

(58) Field of Classification Search
CPC .................................. Y10S 71/02; C05D 9/02
See application file for complete search history.

(56) References Cited

U.S. PATENT DOCUMENTS

| 3,198,635 | A | | 8/1965 | Anderson | |
|---|---|---|---|---|---|
| 3,388,989 | A | | 6/1968 | Kamil | |
| 3,900,572 | A | * | 8/1975 | Peer | A23C 21/026 426/41 |
| 3,914,438 | A | | 10/1975 | Holt | |
| 3,983,214 | A | * | 9/1976 | Misato | A01N 37/00 514/53 |
| 4,009,263 | A | | 2/1977 | Shafer | |
| 4,009,264 | A | | 2/1977 | Mizutani | |
| 4,319,910 | A | * | 3/1982 | Meyer | 71/27 |
| 4,326,523 | A | | 4/1982 | Wolfrom et al. | |
| 4,551,164 | A | * | 11/1985 | Tenzer | C05F 11/08 71/6 |
| 5,110,965 | A | | 5/1992 | Thunberg et al. | |
| 5,186,738 | A | | 2/1993 | Wendt et al. | |
| 5,504,055 | A | * | 4/1996 | Hsu | A01N 59/06 504/121 |
| 5,549,729 | A | | 8/1996 | Yamashita | |
| 5,591,878 | A | | 1/1997 | Nelson et al. | |
| 5,707,679 | A | | 1/1998 | Nelson | |
| 5,759,226 | A | * | 6/1998 | Herold | C05G 3/0064 556/134 |
| 5,797,976 | A | * | 8/1998 | Yamashita | A01G 7/06 71/11 |
| 5,846,581 | A | | 12/1998 | Catron | |
| 5,882,685 | A | | 3/1999 | Ashmead | |
| 6,033,689 | A | | 3/2000 | Waterman et al. | |
| 6,293,045 | B1 | * | 9/2001 | Morgan | C09K 17/52 47/1.01 F |
| 6,352,706 | B1 | * | 3/2002 | Puritch | A01N 25/008 424/405 |
| 2001/0001996 | A1 | | 5/2001 | Shirataki et al. | |
| 2001/0015363 | A1 | | 8/2001 | Rahmey | |
| 2001/0019996 | A1 | | 9/2001 | Soula et al. | |
| 2004/0050126 | A1 | * | 3/2004 | Green | 71/31 |
| 2004/0097372 | A1 | | 5/2004 | Abraham et al. | |
| 2004/0121914 | A1 | * | 6/2004 | Catalano | A01N 37/44 504/322 |
| 2004/0228928 | A1 | | 11/2004 | Zeigler | |
| 2005/0281792 | A1 | | 12/2005 | Short et al. | |

(Continued)

FOREIGN PATENT DOCUMENTS

CA 2278383 1/2001
CA 2718211 9/2009
(Continued)

OTHER PUBLICATIONS

EPO Translation of Umizaki, JP2000226303, assessed on Apr. 7, 2015.*
Hamza et al., Turf Grass Trends, pp. 6-10 (2001).*
Shaukat-Ahmed et al., PNAS, 47: 24-36 (1961).*
Stability Constants (log K1) of Various Metal Chelates (2006) downloaded from http://www.coldcure.com/html/stability_constants.html, Oct. 8, 2015.*
Schulte et al., Understanding Plant Nutrients, A2526, 1999 pp. 1-4.*
Gad et al., Research Journl of Agriculture and Biological Sciences, 2: 433-442 (2006).*
Office Action for corresponding Russian Application No. 2012131271/13(049252) dated Jun. 30, 2014.
(Continued)

*Primary Examiner* — Johann R Richter
*Assistant Examiner* — Danielle Sullivan
(74) *Attorney, Agent, or Firm* — Billion & Armitage; Gregory S. Schwartz

(57) ABSTRACT

Embodiments of the invention relate to a method of making a mineral product. The method includes contacting a carboxylic acid and an inorganic mineral compound sufficient to form a solution, reacting the solution over a period of time sufficient to provide a mineral chelated compound, transferring the mineral chelated compound to one or more molds prior to the compound substantially solidifying and reducing the size of the mineral chelated compound sufficient to provide a rapidly soluble mineral chelated product.

18 Claims, 3 Drawing Sheets

(56) References Cited

U.S. PATENT DOCUMENTS

| | | | |
|---|---|---|---|
| 2006/0084573 A1* | 4/2006 | Grech | C05B 7/00 504/101 |
| 2006/0165824 A1* | 7/2006 | Khambe | A61K 36/185 424/769 |
| 2006/0168881 A1* | 8/2006 | Straumietis | A01G 31/00 47/62 R |
| 2006/0240984 A1 | 10/2006 | Pallett et al. | |
| 2007/0065413 A1 | 3/2007 | Castillo | |
| 2007/0232693 A1 | 10/2007 | Abou-Nemeh | |
| 2008/0033196 A1 | 2/2008 | Goh et al. | |
| 2008/0314107 A1* | 12/2008 | Ettlin et al. | 71/27 |
| 2009/0126719 A1* | 5/2009 | Almagro | A23K 1/164 127/55 |
| 2009/0133456 A1* | 5/2009 | Zapata Rivera | C05F 5/008 71/23 |
| 2009/0252827 A1 | 10/2009 | Baginski | |
| 2009/0306121 A1 | 12/2009 | Cook et al. | |
| 2009/0308121 A1 | 12/2009 | Reddy et al. | |
| 2010/0311583 A1 | 12/2010 | Laurent et al. | |
| 2011/0152363 A1 | 6/2011 | Knochenmus et al. | |
| 2011/0201649 A1 | 8/2011 | Matsuzaki et al. | |
| 2014/0011675 A1 | 1/2014 | Knochenmus | |
| 2014/0026629 A1 | 1/2014 | Knochenmus | |

FOREIGN PATENT DOCUMENTS

| | | |
|---|---|---|
| CL | 44783 | 10/2009 |
| CN | 1104625 A | 7/1995 |
| CN | 1344136 A | 4/2002 |
| CN | 1824606 A | 8/2006 |
| CN | 101496556 A | 8/2009 |
| EP | 0945065 A1 | 9/1999 |
| EP | 1795516 A1 | 6/2007 |
| JP | 2000226303 A * | 8/2000 |
| KR | 10-0480681 | 4/2005 |
| RU | 2 268 868 C2 | 1/2006 |
| WO | 1998021166 | 5/1998 |
| WO | 9926898 A1 | 6/1999 |
| WO | 2001038262 A1 | 5/2001 |
| WO | WO 2007069072 A2 * | 6/2007 |
| WO | 2009138761 A1 | 11/2009 |
| WO | 2011078891 A1 | 6/2011 |
| WO | 2014008472 A1 | 1/2014 |
| WO | 2014008472 A2 | 1/2014 |

OTHER PUBLICATIONS

International Search Report (Form PCT/ISA/210) for related International Application No. PCT/US2013/049447 dated Dec. 12, 2013.
Written Opinion (Form PCT/ISA/237) for related International Application No. PCT/US2013/049447 dated Dec. 12, 2013.
International Search Report for corresponding International Application No. PCT/US2010/041848 dated Feb. 23, 2011.
Written Opinion for corresponding International Application No. PCT/US2010/041848 dated Feb. 23, 2011.
International Preliminary Report on Patentability for corresponding International Application No. PCT/US2010/041848 dated Jun. 26, 2012.
Office Action for corresponding Chinese application No. 201080063204.X dated Apr. 8, 2013.
Wang, Maorong, "Effect of microelement copper, iron, iodine, moybdenum on fermentation of rumen microbe," (Dec. 31, 2003) Animal Feed Journal: 23-26.
Long et al., "Effect of multi-element organic complex fertilizer on increasing the yields of cole plant," Southwest China Journal of Agricultural Sciences (Dec. 31, 2004) 17 (4): 538-540.
Office Action for corresponding New Zealand application No. 601352 dated Mar. 12, 2013, 3 pp.
SMART! Chelate Fertilizers <http://www.smart-fertilizer.com/articles/chelate-fertilizers> Aug. 29, 2007, retrieved online Mar. 18, 2013, 1 pp.
Role of chelated trace minerals in animal production <www.neospark.com/images/CHELATED.PDF> Sep. 30, 2002, 2 pp.
Standard Process, Maganese B12 <https://www.standardprocess.com/Standard-Process-Document-Library/Product-Detail-Sheets/maganeseb125490.pdf> Apr. 15, 1999, 2 pp.
Office Action for corresponding Australian application No. 2010333959 dated Jun. 21, 2013, 4 pp.
"Standard Process, Manganese B12", https://www.standardprocess.com/Standard-Process-Document-Library/Product-Detail-Sheets/maganeseb125490.pdf, Apr. 15, 1999, 2 pages.
Das, et al., "Biosorption of heavy metals—An overview", Indian Journal of Biotechnology, vol. 7, Apr. 2008, pp. 159-169.
Deepatana, et al., "Steric hindrance effect on adsorption of metal-organic complexes onto aminophosphonate chelating resin", Desalination, vol. 218, 2008, pp. 297-303.
Farooq, et al., "Micronutrient application through seed treatments—a review", Journal of Soil Science and Plant Nutrition, vol. 12 (1), 2012, pp. 1-14.
Gad, et al., "Barley response to salt stress at varied levels of cobalt II. Some physiological and chemical characteristics", Journal of Applied Sciences Research, vol. 7 (11), 2011, pp. 1447-1453.
Gad, et al., "Influence of cobalt and phosphorus on growth, yield quantity and quality of sweet potato (*Ipomoea batatas* L)", Journal of Applied Sciences Research, vol. 7 (11), 2011, pp. 1501-1506.
Gad, et al., "Influence of cobalt and phosphorus uptake, growth and yield of tomato", Agriculture and Biology Journal of North America, vol. 1 (5), 2010, pp. 1069-1075.
Gad, et al., "Maximizing the tolerance of wheat plants to soil salinity using cobalt 2—some physiological and chemical characteristics", Journal of Applied Sciences Research, vol. 7 (11), 2011, pp. 1551-1557.
Jaleel, et al., "Effect of soil applied cobalt on activities of antioxidant enzymes in Arachis hypogaea", Global Journal of Molecular Sciences, vol. 3 (2), 2008, pp. 42-45.
Jaleel, et al., "Low concentration of cobalt increases growth, biochemical constituents, mineral status and yield in *Zea mays*", Journal of Scientific Research, vol. 1 (1), 2009, pp. 128-137.
Jayakumar, et al., "Changes in growth, biochemical constituents, and antioxidant potentials in radish (*Raphanus sativus* L) under cobalt stress", Turk. J. Biol., vol. 31, 2007, pp. 127-136.
Jayakumar, et al., "Uptake and accumulation of cobalt in plants: a study based on exogenous cobalt in soybean", Botany Research International, vol. 2 (4), 2009, pp. 310-314.
Johnson, et al., "A cobalt requirement for symbiotic growth of azolla filiculoides in the absence of combined nitrogen", Plant Physiol., vol. 41, 1966, pp. 852-855.
Palit, et al., "Effects of cobalt on plants", The Botanical Review, vol. 60 (2), Apr.-Jun. 1994, pp. 149-181.
Pothalkar, "Key to physiological investigations on drought tolerance in Pigeonpea (*Cajanus cajan* L)", Thesis submitted to the University of Agricultural Sciences, Dharwad in partial fulfillment of the requirements for the Degree of Doctor of Philosophy in Crop Physiology, Apr. 2007, pp. 1-122.
Quintao Lana, et al., "Cobalt and molybdenum concentrated suspension for soybean seed treatment", R. Bras. Ci. Solo, vol. 33, 2009, pp. 1715-1720.
Robinson, et al., "Soil amendments affecting nickel and cobalt uptake by Berkheya coddii: Potential use for phytomining and phytoremediation", Annals of Botany, vol. 84, 1999, pp. 689-694.
Extended European Search Report for European Application No. 13813126.3 dated Nov. 12, 2015, 7 pages.
PCT/US2015/026495, "International Search Report" for related International Application No. PCT/US2015/026495, dated Jul. 8, 2015, 5 pages.
PCT/US2015/026495, "Written Opinion" for related International Application No. PCT/US2015/026495, dated Jul. 8, 2015, 5 pages.
Non-Final Office Action dated Apr. 4, 2017, issued by the USPTO in U.S. Appl. No. 14/689,991, 20 pp.

(56) References Cited

OTHER PUBLICATIONS

Communication pursuant to Article 94(3) EPC dated Mar. 1, 2017, issued by the European Patent Office in EP Patent Application No. 13813126.3, 3 pp.
Office Action for corresponding Canadian Application No. 2,877,981.

* cited by examiner

ORGANICALLY CHELATED MINERAL COMPOSITIONS AND METHODS THEREOF

CROSS-REFERENCE TO RELATED APPLICATION

This application is a divisional application of U.S. patent application Ser. No. 12/835,545, filed on 13 Jul. 2010, which claims priority under 35 U.S.C. § 119(e) to U.S. Provisional Patent Application No. 61/289,295 filed Dec. 22, 2009, which is incorporated herein by reference in its entirety.

BACKGROUND

Cobalt and other inorganic minerals are useful to mammals in many ways. One important need for cobalt in animal nutrition is in regard to vitamin B12 production. Microorganisms require cobalt to produce vitamin B12. Digestive bacteria have a very strong affinity for cobalt. When a dissociable cobalt source is introduced into the rumen, for example, the uptake by bacteria is rapid—about 80-85% within 30-40 minutes. The plant form of cobalt supplied by ration ingredients is released with a considerable degree of variability. So, matching the form provided in a supplement to the metabolic demands by the rumen microorganisms and the animals' physiological needs is key to maximizing animal performance.

Vitamin B12 levels in an animal are directly proportional to the level of available cobalt supplied to the rumen. Vitamin B12 levels in the plasma and liver directly impact the ability to convert propionic acid to glucose and the ability to synthesize methionine. Products on the market to supply cobalt to animals or other living organisms are often in forms less available to the animal or organism than desirable, causing unnecessary waste and inefficiencies. Conventional processes of making such products are inefficient and impractical to provide a soluble form. There is a marked difference in solubility in water of cobalt lactate versus cobalt carbonate, for example.

Cobalt, transition metals and trace minerals are useful to microorganisms directly for metabolism, immune function and reproduction. Microorganisms in the soil that fix nitrogen to enhance plant growth are called Azotobacters. The form of the trace minerals added to soil or to other systems employing microorganisms, such as waste treatment systems, biofilters, anaerobic digestors and the like, impacts the availability and therefore uptake of the trace element.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Figure 1:
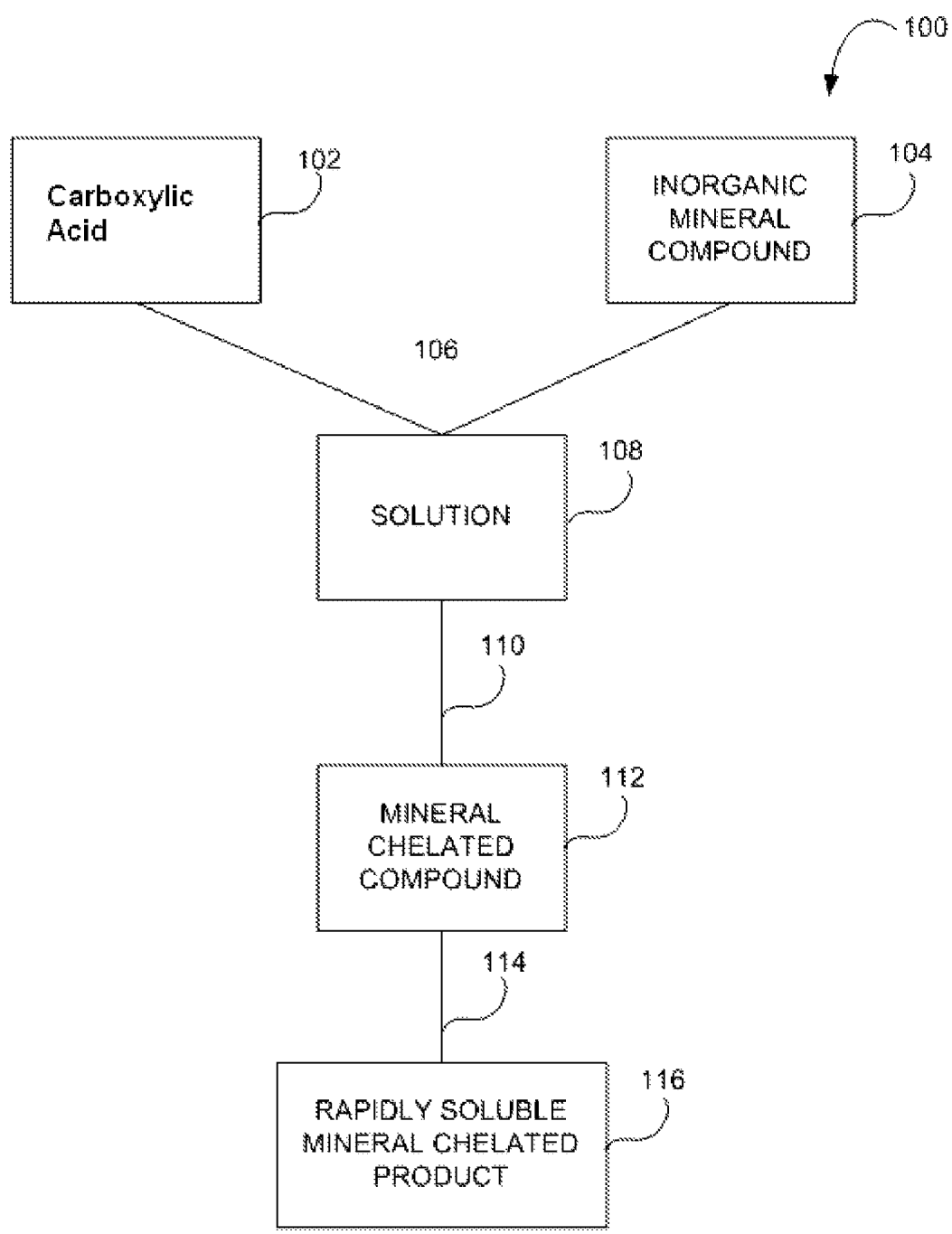
FIG. 1 illustrates a block flow diagram of a method of making a rapidly soluble mineral chelated product, according to some embodiments.

Embodiments of the invention relate to a method of making a mineral product. The method includes contacting a carboxylic acid and an inorganic mineral compound sufficient to form a solution, reacting the solution over a period of time sufficient to provide a mineral chelated compound, transferring the mineral chelated compound to one or more molds prior to the compound substantially solidifying and reducing the size of the mineral chelated compound sufficient to provide a rapidly soluble mineral chelated product.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the invention relate to inorganic mineral chelated compositions and methods of making and using such compositions. Embodiments describe a unique process including a reaction to form an organically bound cobalt or other mineral, optionally carrying the reacted material in an inert media and applying or administering the product. The process is substantially stoichiometric, in which there are little to no by-products that would otherwise need to be removed from the product. The process is very efficient, cost-effective and provides a readily available form of inorganic material for fertilization or nutrition or the benefit of microflora in a number of applications. The composition produced may be in a liquid form that is easily applied to plants, pastures, lawns or gardens or administering via a nutritional product or feed to animals or humans. Embodiments of the present invention utilize a carboxylic acid, such as lactic acid, to provide an inorganic mineral chelated composition that is easily administered or applied in any form or supplementation, liquid nutrition, agricultural use or industrial use.

In supplementation, the composition has a greater affinity to digestive microbials than other sources or structures of inorganic minerals. In ruminants, for example, the composition provides faster weight gain, heavier weaning weights and enhances rumen fermentation utilization. The composition increases cellulose breakdown and utilization and helps digest forage better. Additionally, the animals utilize protein and calcium better, providing a decreased need for commercial proteins.

In addition to administering the chelated compound to mammals or other living organisms as part of feed or feed supplement, methods of applying the product for agricultural purposes are described. It is possible to transfer nutrients to a mammal through treatment of the soil or plants on which it grazes. This may be more cost effective and potentially more efficacious to the animal. Additionally, chelated trace minerals such as cobalt positively impact the health and growth of microorganisms, thus having a beneficial impact on the microorganisms' environment.

Definitions

As used herein, "fatty acid" refers to a carboxylic acid, often with a long unbranched aliphatic tail (chain), which may be either saturated or unsaturated. Examples of fatty acids may include lactic acid, propionic acid and butyric acid.

As used herein, "carboxylic acid" refers to organic acids characterized by the presence of a carboxyl group, which has the formula —C(=O)OH, usually written —COOH or —CO$_2$H. Examples of carboxylic acids may include lactic acid, propionic acid and butyric acid.

As used herein "microflora" refers to living microorganisms that are so small that they can be seen only with a microscope and that maintain a more or less constant presence in a particular area, e.g. the pharynx or the rumen. Microflora includes bacteria, viruses, protozoa and fungi for example.

As used herein, "lactic acid" refers to a carboxylic acid with a chemical formula of $C_3H_6O_3$.

As used herein, "inorganic mineral compound" refers to an elemental or compound composition including one or more inorganic species. For example, an inorganic mineral compound may be cobalt, cobalt carbonate, zinc oxide, cupric oxide, manganese oxide or a combination thereof. Inorganic mineral compounds may include scandium, selenium, titanium, vanadium, chromium, manganese, iron, nickel, copper and zinc, for example. Transition metals may also be included and salts, oxides, hydroxides and carbonates of the above mentioned compounds may be used.

As used herein, "solution" refers to a homogeneous or substantially homogeneous mixture of two or more substances, which may be solids, liquids, gases or a combination thereof.

As used herein, "reacting" refers to undergoing a chemical change. Reacting may include a change or transformation in which a substance decomposes, combines with other substances, or interchanges constituents with other substances As used herein, "mineral chelated compound" refers to chemical compound or mixture including at least one inorganic substance and a derivative of a carboxylic acid or reaction product of a carboxylic acid and an inorganic mineral compound.

As used herein, "transferring" refers to moving a component or substance from one place or location to another.

As used herein, "mold" refers to a hollow form or matrix for shaping a fluid, gel, semi-solid or plastic substance.

As used herein, "filtering" or "filtration" refers to a mechanical method to separate solids from liquids, or separate components by size or shape. This can be accomplished by gravity, pressure or vacuum (suction).

As used herein, "rapidly soluble mineral chelated product" refers to a mineral chelated compound that has been altered to increase solubility in a solvent. Altering may include reducing in size, filtering, screening or chemically reacting. An inorganic mineral compound may be organically chelated such that its solubility changes from insoluble to soluble in a chose solvent.

As used herein, "screening" refers to separating components by size by passing or refusing to pass components through a screen or mesh.

As used herein, "reducing in size" refers to physically or chemically reducing the size of one or more components, such as by grinding, crushing or milling, for example.

As used herein, "mesh size" refers to the number of openings in one inch of a screen or filter.

As used herein, "contacting" may refer to physically, chemically, electrically touching or bringing within sufficient close proximity.

As used herein, "carrier" refers to a substance physically or chemically bound with a target or active substance in order to facilitate the use or application of the target or active substance.

As used herein, "substrate" refers to a base layer or material on which an active or target material interacts with, is applied to or is carried by.

As used herein, "stoichiometric" or "stoichiometric amounts" refer to starting materials of a reaction having molar amounts or substantially molar amounts such that the reaction product is formed with little to no unused starting material or waste. A stoichiometric reaction is one in which all starting materials are consumed (or substantially consumed) and converted to a reaction product or products.

As used herein, "applying" refers to bringing one or more components into nearness or contact with another component.

As used herein, "administering" refers to giving or applying. More specifically, administering refers to providing a substance such a mammal ingests the substance, such as through feeding or medication.

As used herein, "feed" refers to food for animals, fish, reptiles, microflora, insects, birds or any living organism.

As used herein, "feed supplement" refers to something added to a feed or food to remedy a deficiency, strengthen or increase the value of the feed or food.

As used herein, "mixture" refers to a combination of two or more substances in physical contact with one another. For example, components of a mixture may be physically combined as opposed to chemically reacting.

Referring to FIG. 1 a block flow diagram 100 of a method of making a rapidly soluble mineral chelated product is shown, according to some embodiments. A carboxylic acid 102, such as lactic acid, may be contacted 106 with an inorganic mineral compound 104, sufficient to form a solution 108. The solution 108 may be reacted 110 over a period of time, sufficient to provide a mineral chelated compound 112. The mineral chelated compound 112 may then be transferred and reduced in size 114 to sufficient to provide a rapidly soluble mineral chelated product 116. Transferring may include transferring to one or more molds, prior to the compound substantially solidifying.

Carboxylic acid 102 may be contacted 106 with an inorganic mineral compound 104, such as by mixing. The molar amounts or stoichiometric amounts may be utilized. If the carboxylic acid 102 is lactic acid, the carboxylic acid content may be about 60% to about 80% of the mixture by weight. The inorganic mineral compound 104 may include about 20% to about 40% of the mixture by weight. More specifically, the lactic acid may include about 62% to about 76% and the inorganic mineral compound 104 may include about 24% to about 38% by weight of the mixture. The lactic acid 102 may be 88% strength lactic acid, for example.

When the carboxylic acid 102 is propionic acid, the carboxylic acid content may be about 55% to about 75% by weight and the inorganic mineral compound content about 25% to about 45% by weight. More specifically, the propionic acid may include about 57% to about 72% and the inorganic mineral compound 104 may include about 28% to about 43% by weight. When the carboxylic acid 102 is butyric acid, the carboxylic acid content may be about 60% to about 80% by weight and the inorganic mineral compound content about 20% to about 40% by weight. More specifically, the butyric acid may include about 61% to about 76% and the inorganic mineral compound 104 may include about 24% to about 39% by weight.

The carboxylic acid 102 and inorganic mineral compound 104 may be placed in a vessel, optionally with one or more catalysts. Examples of a catalyst include iron and alkaline earth metals. The vessel may be optionally agitated, such as by vibrating, shaking, turning or spinning. Water may be added to the vessel, before, during or after the contacting 106 of carboxylic acid 102 and inorganic mineral compound 104. Once a solution 108 is formed, it may be reacted 110 over a period of time. The reaction may initiate based solely on the contact 106 between carboxylic acid 102 and inorganic mineral compound 104, after addition or contact with a catalyst or similarly with the contact or addition of water of some combination thereof. Depending on the type of inorganic mineral compound utilized 104, carbon dioxide may be evolved as the solution 108 heats up. Both water vapor and optionally carbon dioxide may be generated and released from the vessel. No reflux process is needed or desired, as often used conventionally with regard to related reactions. All by-products may be passively and naturally removed, without the need for solvent or refluxing. Carbon dioxide and water may be released into the atmosphere, for example.

The reaction ultimately produces a mineral chelated compound 112. The mineral chelated compound 112 may form a porous, brittle rock if left to solidify. The mineral chelated compound 112 may then be transferred from the vessel to one or more molds, prior to the compound substantially solidifying. The molds may be of varying shapes or sizes, such that the compound may be easily handled and transported. Water vapor may be further driven off the compound as it solidifies within the one or more molds.

The mineral chelated compound 112 may be reduced in size 114. The compound 112 may be removed from the molds and placed in a "de-lumper" or single or double shaft disintegrator or crusher, which may reduce the size of the compound to small particles. The particles may be about 1 to about 2 inches in size, for example. The small particles may then be further reduced in size 114, such as by being contacted with a mill (i.e., hammer mill or roller mill). The small particles may then be reduced to a fine powder. Reducing the compound 112 to a fine powder may increase its solubility, providing a rapidly soluble mineral chelated product 116. After contacting with a mill, the particles may be screened to further separate larger particles from smaller ones. Any larger particles may be placed back in the mill for further reduction in size. Screening may include filtering with a mesh. The mesh size may be about 50 to about 70 or about 50, about 60 or about 70 size mesh. The mesh size may less than 50 for example.

The rapidly soluble mineral chelated product 116 may be further contacted with a carrier. The carrier may be a dry substrate or a liquid carrier, for example. The carrier may include one or more of diatomaceous earth, calcium carbonate, limestone, sugars, dextrose, water, ground corn cobs, starch and combinations thereof.

One example of the rapidly soluble mineral chelated product 116 may be organically chelated cobalt, with the following chemical formula:

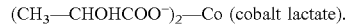

$(CH_3—CHOHCOO^-)_2—Co$ (cobalt lactate).

Figure 2:
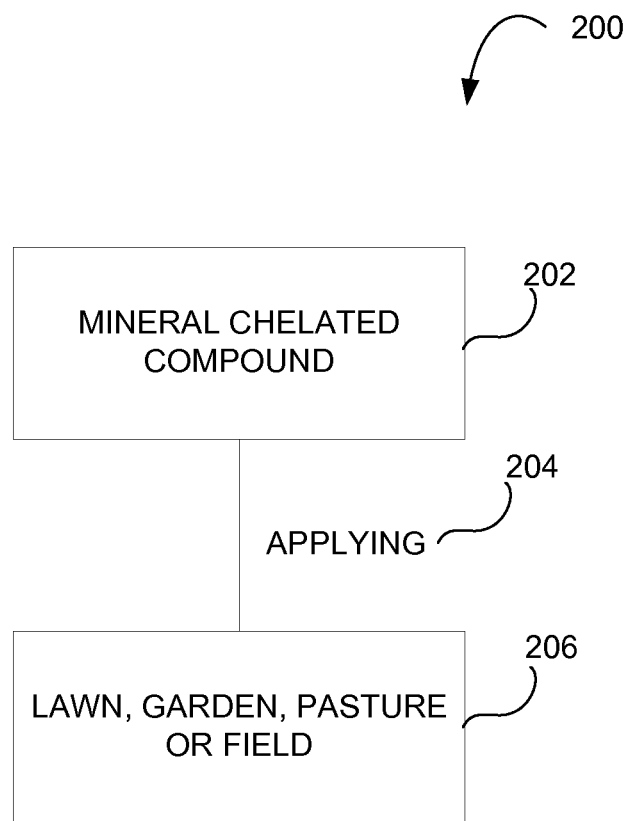
FIG. 2 illustrates a block flow diagram of a method of applying a mineral lactate compound, according to some embodiment.
Figure 3:
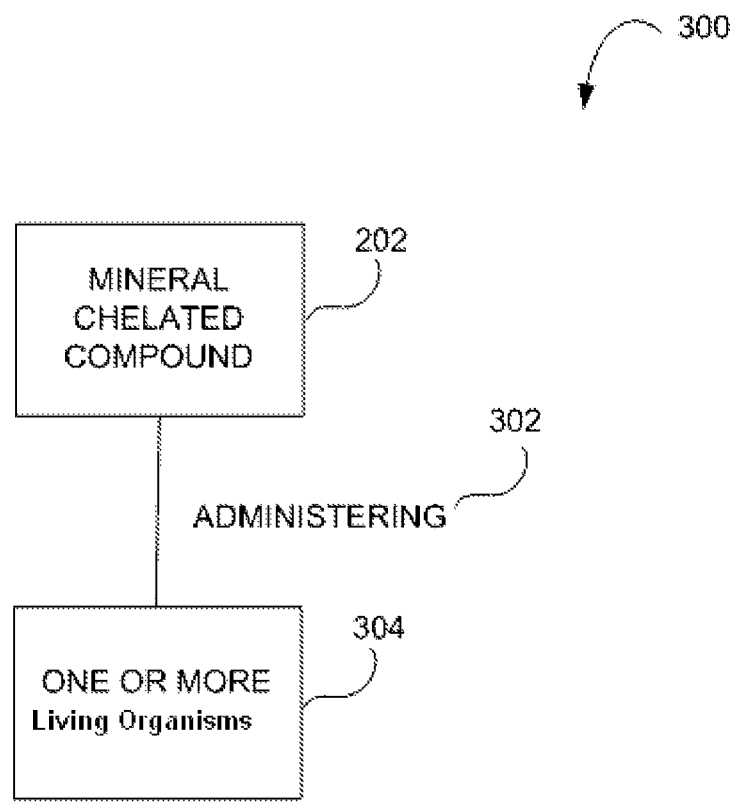
FIG. 3 illustrates a block flow diagram of a method of administering a mineral lactate compound, according to some embodiment.

Referring to FIG. 2, a block flow diagram 200 of a method of applying a mineral chelated compound is shown, according to some embodiment. A mineral chelated compound 202 may be applied 204 to a lawn, garden, pasture or field 206, for example. Alternatively, the compound 202 may be administered 302 to one or more living organisms 304 (see view 300 of FIG. 3). The compound 202 may further include a carrier.

The compound 202 may include one or more of a cobalt lactate compound, zinc lactate compound, copper lactate compound or manganese lactate compound. The carrier may include diatomaceous earth. Applying 204 may include spraying, planting in a seed mix, planting in a fertilizer mix, or a combination thereof. Lawn, garden, pasture or field 206 may include sporting fields and golf courses, for example. Pasture or field may include a harvested field, bailed field, or field or pasture with crops cut. Applying 204 may also include applying while the crop is harvested or after the crop is harvested. Applying 204 may increase growth in a plant. Applying 204 may include applying the compound 202 in an amount between about 1 to about 100 ppm or between about 1 to about 1000 ppm, for example. The compound 202 may also be used as a benefit to any microflora, enzyme or biological industrial product, for example. The compound 202 may be used industrially or in human nutrition. Applying 204 may strengthen a root system of a plant.

The one or more living organisms may include mammals, such as monogastric or ruminant mammals. Administering 204 may include providing the product as a feed or feed supplement. Alternatively, administering 204 may include providing the product to the mammals through ingestion of a plant containing the product. Administering 304 may increase rumen activity in a mammal, for example. Increasing rumen activity may include increasing metabolism.

The mineral product discussed in embodiments of the current invention may include one or more mineral chelated lactates in addition to other components. The mineral product may include one or more metal sulfates, such as sulfates of manganese, zinc, copper or combinations thereof. The one or more mineral chelated lactates may be a cobalt lactate compound, zinc lactate compound, copper lactate compound or manganese lactate compound. A carrier may be utilized, such as dextrose. Additional components may include fibers, *yucca* and one or more enzymes.

The one or more mineral chelated lactates may be present in an amount of about 15% to about 20% of the product by weight. The one or more metal sulfates may be present in an amount of about 2% to about 10% of the product by weight. The fiber may be present in an amount of about 1% to about 5% of the product by weight. The enzymes may include about 0.1% to about 2% by weight, the *yucca* about 1% to about 5% by weight and the carrier about 60% to about 80% by weight.

Example 1

In Table 1, the growth of grass when cobalt lactate was applied either in the soil (before seeding) or sprayed directly onto the grass once growing is shown for the various levels of cobalt (0, 1, 10, 100 and 1000 ppm) that was applied. Following growth 2, cuttings were made then the total weight of grass was shown for the various treatments. Growth roughly doubled when cobalt lactate was applied in the soil at 1 or 10 ppm or applied by spray at 100 ppm. All work was done with a fully complete soil with respect to nitrogen, phosphorus and potash (Miracle Gro Soil), so that the only difference in the greenhouse flats was the applied cobalt level and the manner in which it was applied. The uptake of cobalt correlated with the application rate and that was mirrored closely at the lower levels.

TABLE 1

| Sample | Cobalt Medium | Soil Weight (gms) | Seed Weight (gms) | Target Cobalt Level (ppm) | Grass Cuttings Weight (gms, 1st) | Grass Cuttings Weight (gms, 2nd) | Sum Grass Cuttings Weight (gms, 1st + 2nd) |
|---|---|---|---|---|---|---|---|
| 1 | Soil | 2550 | 2.6 | 0 | 19.94 | 3.31 | 23.25 |
| 2 | Soil | 2550 | 2.6 | 1 | 31.06 | 22.73 | 53.79 |
| 3 | Soil | 2550 | 2.6 | 10 | 22.8 | 31.41 | 54.21 |
| 4 | Soil | 2550 | 2.6 | 100 | 16.33 | 10.12 | 26.45 |
| 5 | Soil | 2550 | 2.6 | 1000 | 5.15 | 1.81 | 6.96 |
| 6 | DI H2O | 2550 | 2.6 | 0 | 17.28 | 8.28 | 25.56 |
| 7 | DI H2O | 2550 | 2.6 | 1 | 15.7 | 13.9 | 29.6 |
| 8 | DI H2O | 2550 | 2.6 | 10 | 17.76 | 14.37 | 32.13 |
| 9 | DI H2O | 2550 | 2.6 | 100 | 18.56 | 26.57 | 45.13 |
| 10 | DI H2O | 2550 | 2.6 | 1000 | 24.03 | 15.44 | 39.47 |

Example 2

Sixty-four sample flats were analyzed. Empty flats were filled with about 0.25 cubic feet of Miracle Gro Soil per flat (a complete soil with enough macro-nutrients, nitrogen, phosphorus and potash to feed the plants for 3-4 months). The seeds were planted and then the seeded soil treated. Flats were watered daily. Progress was documented weekly. This number of flats resulted from running a number of positive controls and several levels of the chelated cobalt lactate per plant selection or choice.

The makeup of 64 flats was 8 sections times 8 flats per section. The first 8 flats were planted with a mixture of clovers. Flats 9-16 were also planted with the clover mixture at 5.2 grams seed/flat versus 2.6 grams seed/flat in 1-8. Flats 17-24 were planted with Fast & Fine Seed at 2.6 grams/flat, equivalent to the seeding rate from 2008. Fast & Fine Premium Grass Seed is a commercial mixture of Indy Perennial Ryegrass, Silver Dollar Perennial Ryegrass, Boreal Creeping Red Fescue, Kelly Kentucky Bluegrass and Clearwater Kentucky Bluegrass. Flats 25-32 were planted with a mixture including green globe turnips, dwarf Essex forage rapeseed, Rangi forage and giant rapeseed. Flats 33-40 were planted with a mixture of seeds including hybrid sunflower, grain sorghum, Proso millet and buck-wheat, at 5.2 grams/flat. Flats 41-48 were planted with Vernal alfalfa at 5.2 grams/flat and 49-56 with the same seed but at 2.6 grams/flat.

Treatment sequence was the same within each of the above 7 sections of flats numbered 1-56. In each section the first flat was the true control, no additional soil additives. The second flat was treated with a commercial soil additive called Delt Ag, the third another product called Plot Max and the fourth with a *Yucca* extract. Delt Ag Seed Coat is a blend of organically complexed nutrients and is specifically designed to enhance seedling emergence and plant growth. It contains sulfur, soluble manganese and soluble zinc (from manganese sulfate and zinc sulfate. It is applied directly to the seed before planting. Plot Max is a commercial product sold by Antler King (Wisconsin). It comprises a liquid product diluted in water and applied to new or existing food plots in the spring or fall. Food plots are areas of forage that farmers keep for wild game such as deer. The active ingredient in Plot Max is humic acid (2%). The fifth, sixth and seventh flats were treated with cobalt lactate in combination with inorganic minerals (matching some of the positive control commercial product inorganic mineral selections) but at increasing levels. The last flat in each section was treated with chelated minerals, cobalt, zinc, copper and manganese lactate.

The flats were maintained daily and no other intervention was made, other than accommodating for plant sun/shade tolerance differences and weeding as necessary.

TABLE 2

64 Flats, 2 Sq Ft/Flat
Miracle-Gro Garden Soil Composite
Each Flat, 0.25 CUFT soil Soil Analysis

| Flat Number | 1-56 | 1 | 2 | 3 | 4 | 5 | 6 | 7 | 8 |
|---|---|---|---|---|---|---|---|---|---|
| Seed Type | | Food Plot Clover Mix | Food Plot Clover Mix | Food Plot Clover Mix | Food Plot Clover Mix | Food Plot Clover Mix | Food Plot Clover Mix | Food Plot Clover Mix | Food Plot Clover Mix |
| Seed Planted (grams) | | 2.6 | 2.6 | 2.6 | 2.6 | 2.6 | 2.6 | 2.6 | 2.6 |
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 125 | 125 | 125 | 125 | 125 | 125 | 125 | 125 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | Cobalt Lactate Mineral Complex II |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |
| Solution (grams/mls H2O) | | Water only | 0.083/1000 | 0.882/1000 | 0.5/1000 | 0.23/1000 | 0.574/1000 | 0.5682/1000 | 0.574/1000 |
| Applied (solution in H2O) | | Water (placebo) | 10 ml in 600 | 100 ml in 600 | 100 ml in 600 | 10 ml in 600 | 10 ml in 600 | 100 ml in 600 | 10 ml in 600 |
| 2nd Part (grams/mls H2O) | | | | | | | | | 0.069/1000* |
| Applied (solution in H2O) | | | | | | | | | 10 ml in 600 |
| 2nd Part Description | | | | | | | | | *3% min lactate |
| 2nd Part Chelated Minerals | | | | | | | | | Mn, Zn, Cu |
| Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | 5 |
| Organic zinc | | | | | | | | | 5 |
| Organic copper | | | | | | | | | 5 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 3 | 3 | 3 | 3 | 3 | 3 | 3 | 3 |
| Plant Harvest Date | | Aug. 19, 2009 | Aug. 19, 2009 | Aug. 19, 2009 | Aug. 19, 2009 | Aug. 19, 2009 | Aug. 19, 2009 | Aug. 19, 2009 | Aug. 19, 2009 |
| Age at Harvest (days) | | 39 | 39 | 39 | 39 | 39 | 39 | 39 | 39 |
| Weight (gms, as-is) | | 66.5 | 201.66 | 268.57 | 261.55 | 203.43 | 223.55 | 302.69 | 247.87 |
| % of Control | | 100 | 303.25 | 403.86 | 393.31 | 305.91 | 336.17 | 455.17 | 372.74 |
| Soil Analysis (dry weight) | | Not submitted | Not submitted | Not submitted | Not submitted | Not submitted | Not submitted | Not submitted | Not submitted |
| Moisture (%) | 52.91 | | | | | | | | |
| pH | 7.1 | | | | | | | | |
| Aerobic Plate Count (Mcfu/g) | 2.4 | | | | | | | | |
| Anaerobic Plate Count (Mcfu/g) | 0.1 | | | | | | | | |
| Azotobacter (Mcfu/g) | 3 | | | | | | | | |
| Microbial Activity (ug/10 g soil/day) | 245 | | | | | | | | |
| Total Nitrogen (N, %) | 1.13 | | | | | | | | |
| Ammonia Nitrogen (%) | 0 | | | | | | | | |
| Nitrate Nitrogen (%) | nd | | | | | | | | |
| Organic Nitrogen (%) | 1.06 | | | | | | | | |
| Phosphorus (P2O5, %) | 0.23 | | | | | | | | |
| Potassium (K2O, %) | 0.25 | | | | | | | | |
| Sulfur (S, %) | 0.36 | | | | | | | | |
| Calcium (Ca, %) | 4.44 | | | | | | | | |
| Magnesium (Mg, %) | 1.83 | | | | | | | | |
| Sodium (Na, %) | 0.02 | | | | | | | | |
| Copper (Cu, ppm) | nd | | | | | | | | |
| Iron (Fe, ppm) | 7539 | | | | | | | | |

TABLE 2-continued

64 Flats, 2 Sq Ft/Flat
Miracle-Gro Garden Soil Composite
Each Flat, 0.25 CUFT soil Soil Analysis

| Flat Number | 1-56 | 1 | 2 | 3 | 4 | 5 | 6 | 7 | 8 |
|---|---|---|---|---|---|---|---|---|---|
| Manganese (Mn, ppm) | 200 | | | | | | | | |
| Zinc (Zn, ppm) | 65.8 | | | | | | | | |
| Total salts (per ton) | 3.61 | | | | | | | | |
| Total Carbon (%) | 25.63 | | | | | | | | |
| C/N Ratio | 22.8:1 | | | | | | | | |
| Chloride | nd | | | | | | | | |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |
| Plant Cuttings mixed forage (DW basis) | | | | | | | | | |
| Moisture (%) | | 85.22 | 85.35 | 85.89 | 85.82 | 85.75 | 83.38 | 84.88 | 83.96 |
| Dry Matter (%) | | 14.78 | 14.65 | 14.11 | 14.18 | 14.75 | 16.62 | 15.17 | 16.04 |
| Crude Protein (%) | | 12.6 | 12.4 | 12.9 | 12.4 | 13.5 | 12.6 | 11.8 | 12.3 |
| Crude Fat (%) | | | | | | | | | |
| Acid Detergent Fiber (%) | | 35.2 | 35.1 | 35.3 | 37.5 | 40.4 | 33 | 35.5 | 40.3 |
| Ash (%) | | | | | | | | | |
| Total digestible nutrients (%) | | 62.4 | 62.5 | 62.3 | 59.8 | 56.5 | 64.9 | 62.1 | 56.6 |
| Net energy- lactation (Mcal/lb) | | 0.64 | 0.64 | 0.64 | 0.61 | 0.57 | 0.67 | 0.64 | 0.58 |
| Net energy- maint. (Mcal/lb) | | 0.62 | 0.62 | 0.62 | 0.59 | 0.55 | 0.65 | 0.61 | 0.55 |
| Net energy- gain (Mcal/lb) | | 0.34 | 0.34 | 0.34 | 0.35 | 0.32 | 0.38 | 0.34 | 0.32 |
| Digestible Energy (Mcal/lb) | | | | | | | | | |
| Metabolizable energy (Mcal/lb) | | | | | | | | | |
| Sulfur (%) | | 0.57 | 0.55 | 0.59 | 0.5 | 0.54 | 0.5 | 0.55 | 0.47 |
| Phosphorus (%) | | 0.52 | 0.34 | 0.36 | 0.29 | 0.32 | 0.29 | 0.33 | 0.29 |
| Potassium (%) | | 4.61 | 5.2 | 5.37 | 4.39 | 4.45 | 4.26 | 4.96 | 4.7 |
| Magnesium (%) | | 1.04 | 1 | 0.94 | 0.86 | 0.83 | 1.03 | 0.99 | 0.84 |
| Calcium (%) | | 2.09 | 1.94 | 1.87 | 1.82 | 1.97 | 2.08 | 2.11 | 1.75 |
| Sodium (%) | | 0.07 | 0.09 | 0.1 | 0.08 | 0.08 | 0.07 | 0.08 | 0.07 |
| Iron (ppm) | | 69 | 64 | 65 | 59 | 64 | 62 | 60 | 63 |
| Manganese (ppm) | | 18 | 19 | 17 | 23 | 23 | 23 | 24 | 19 |
| Copper (ppm) | | 7 | 5 | 6 | 5 | 6 | 6 | 7 | 5 |
| Zinc (ppm) | | 106 | 89 | 80 | 81 | 92 | 85 | 89 | 81 |
| Cobalt (ppm) | | 1.8 | 0.9 | 0.51 | 0.49 | 0.48 | 0.36 | 0.38 | 0.26 |

The Delt Ag flat may be considered the control. Regardless, the flat with the highest growth was Number 7, treated with 1238 grams of a mix of chelated cobalt and inorganic manganese, copper and zinc. Of all the treatments, it had the best response, about 50% ahead of the commercialized Delt Ag soil treatment product that contains minerals but no chelated cobalt. It along with all the other flats in this series was planted at 2.6 grams/flat, the same seeding rate that the 2008 grass was planted at.

Of interest in this series is Number 8 flat, treated with a combination of mineral lactates that include not only cobalt, but manganese, copper and zinc lactates yielding mineral concentrations as shown in the table. This combination is termed cobalt lactate mineral complex 2. Note that the growth was ahead of Number 2 flat, the Delt Ag product.

All of the plants harvested from each section were submitted for forage testing. Mineral uptake by the plants was measured and observed for possible compositional changes in the plants that might lead to differences in plant-available energy/nutrients. Flat 6, treated with chelated minerals, cobalt, zinc, copper and manganese lactate at 125 grams/acre appears to have a meaningful increase in total digestible nutrients.

TABLE 3

64 Flats, 2 Sq Ft/Flat
Miracle-Gro Garden Soil Composite
Each Flat, 0.25 CUFT soil Soil Analysis

| Flat Number | 1-56 | 9 | 10 | 11 | 12 | 13 | 14 | 15 | 16 |
|---|---|---|---|---|---|---|---|---|---|
| Seed Type | | Food Plot Clover Mix | Food Plot Clover Mix | Food Plot Clover Mix | Food Plot Clover Mix | Food Plot Clover Mix | Food Plot Clover Mix | Food Plot Clover Mix | Food Plot Clover Mix |
| Seed Planted (grams) | | 5.2 | 5.2 | 5.2 | 5.2 | 5.2 | 5.2 | 5.2 | 5.2 |
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 249 | 249 | 249 | 249 | 249 | 249 | 249 | 249 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | COBALT LACTATE MINERAL COMPLEX 2 |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |
| Solution (grams/mls H2O) | | Water only | 0.083/1000 | 0.882/1000 | 0.5/1000 | 0.23/1000 | 0.574/1000 | 0.5682/1000 | 0.574/1000 |
| Applied (solution in H2O) | | Water (Placebo) | 10 ml in 600 | 100 ml in 600 | 100 ml in 600 | 10 ml in 600 | 10 ml in 600 | 100 ml in 600 | 10 ml in 600 |
| 2nd Part (grams/mls H2O) | | | | | | | | | 0.069/1000* |
| Applied (solution in H2O) | | | | | | | | | 10 ml in 600 |
| 2nd Part Description | | | | | | | | | *3% min lactate |
| 2nd Part Chelated Minerals | | | | | | | | | Mn, Zn, Cu |
| Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | 5 |
| Organic zinc | | | | | | | | | 5 |
| Organic copper | | | | | | | | | 5 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 3 | 3 | 3 | 3 | 3 | 3 | 3 | 3 |
| Plant Harvest Date | | Aug. 16, 2009 | Aug. 16, 2009 | Aug. 16, 2009 | Aug. 16, 2009 | Aug. 16, 2009 | Aug. 16, 2009 | Aug. 16, 2009 | Aug. 16, 2009 |
| Age at Harvest (days) | | oi | 36 | 36 | 36 | 36 | 36 | 36 | 36 |
| Weight (gms, as-is) | | 132.07 | 231.98 | 193.82 | 248.28 | 261.66 | 207.52 | 184.1 | 96.32 |
| % of Control | | 100 | 175.65 | 146.76 | 187.99 | 198.12 | 157.13 | 139.40 | 72.93 |
| Soil Analysis (dry weight) | | Submitted | Submitted | Submitted | Submitted | Submitted | Submitted | Submitted | Submitted |
| Moisture (%) | 52.91 | 65.3 | 53.7 | 59.26 | 56.3 | 54.22 | 55.7 | 51.94 | 57.64 |
| pH | 7.1 | 7.5 | 7.3 | 7.5 | 7.6 | 7.5 | 7.6 | 7.5 | 7.6 |
| Aerobic Plate Count (Mcfu/g) | 2.4 | 15 | 13 | 14 | 18 | 20 | 7.5 | 10 | 20 |
| Anaerobic Plate Count (Mcfu/g) | 0.1 | 1.2 | 0.32 | 0.63 | 1 | 0.51 | 0.48 | 1.3 | 0.63 |
| Azotobacter (Mcfu/g) | 3 | 125 | 17 | 81 | 31 | 44 | 22 | 62 | 92 |
| Microbial Activity (ug/10 g soil/day) | 245 | 2156 | 1573 | 1754 | 1577 | 2043 | 1699 | 1823 | 1721 |
| Total Nitrogen (N, %) | 1.13 | 1.07 | 1.23 | 1.25 | 1.1 | 1.09 | 1.22 | 1.12 | 1.2 |
| Ammonia Nitrogen (%) | 0 | 0.01 | 0.01 | 0.02 | nd | 0.03 | 0.01 | 0.01 | 0.01 |
| Nitrate Nitrogen (%) | nd | nd | nd | nd | nd | nd | nd | nd | nd |
| Organic Nitrogen (%) | 1.06 | 1.06 | 1.22 | 1.23 | 1.1 | 1.06 | 1.21 | 1.11 | 1.19 |
| Phosphorus (P2O5,%) | 0.23 | 0.32 | 0.3 | 0.27 | 0.25 | nd | 0.27 | 0.25 | 0.28 |
| Potassium (K2O, %) | 0.25 | nd | nd | nd | nd | nd | nd | nd | Nd |
| Sulfur (S, %) | 0.36 | 0.4 | 0.41 | 0.42 | 0.48 | 0.37 | 0.41 | 0.37 | 0.4 |
| Calcium (Ca, %) | 4.44 | 7.72 | 4.41 | 8.2 | 6 | 7.36 | 5.78 | 3.56 | 4.08 |
| Magnesium (Mg,%) | 1.83 | 3.6 | 1.64 | 3.53 | 2.43 | 3.6 | 2.51 | 1.31 | 1.49 |
| Sodium (Na, %) | 0.02 | 0.03 | 0.04 | 0.02 | 0.03 | 0.04 | 0.02 | 0.04 | 0.05 |
| Copper (Cu, ppm) | nd | nd | nd | nd | nd | nd | nd | nd | Nd |
| Iron (Fe, ppm) | 7539 | 7565 | 8475 | 8623 | 7952 | 7237 | 7226 | 7039 | 8050 |
| Manganese (Mn, ppm) | 200 | 245 | 326 | 280 | 220 | 199 | 208 | 198 | 224 |
| Zinc (Zn, ppm) | 65.8 | 86.5 | 90.7 | 85.9 | 107.6 | 67.7 | 74.5 | 81.1 | 111 |

TABLE 3-continued

64 Flats, 2 Sq Ft/Flat
Miracle-Gro Garden Soil Composite
Each Flat, 0.25 CUFT soil Soil Analysis

| Flat Number | 1-56 | 9 | 10 | 11 | 12 | 13 | 14 | 15 | 16 |
|---|---|---|---|---|---|---|---|---|---|
| Total salts (per ton) | 3.61 | 4.3 | 3.39 | 5.3 | 4.17 | 5.54 | 4.22 | 2.9 | 2.89 |
| Total Carbon (%) | 25.63 | 26.6 | 25.01 | 25.85 | 24.87 | 21.91 | 25.37 | 23.85 | 27.41 |
| C/N Ratio | 22.8:1 | 24.9:1 | 20.3:1 | 20.6:1 | 22.6:1 | 20.1:1 | 20.8:1 | 21.2:1 | 22.8:1 |
| Chloride | nd | nd | nd | nd | nd | nd | nd | nd | Nd |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |
| Plant Cuttings mixed forage (DW basis) | | | | | | | | | |
| Moisture (%) | | 86.21 | 83.4 | 87.54 | 85.68 | 87.21 | 88.2 | 88.11 | 86.78 |
| Dry Matter (%) | | 13.79 | 16.6 | 12.46 | 14.32 | 12.79 | 11.8 | 11.89 | 13.22 |
| Crude Protein (%) | | 14.5 | 14.5 | 15.4 | 15.6 | 14.1 | 19.8 | 17.9 | 16.4 |
| Crude Fat (%) | | | | | | | | | |
| Acid Detergent Fiber (%) | | 26.7 | 17.5 | 24.5 | 28 | 24.5 | 37.1 | 33.1 | 34.8 |
| Ash (%) | | | | | | | | | |
| Total digestible nutrients (%) | | 72.1 | 82.6 | 74.6 | 70.6 | 74.6 | 60.2 | 64.8 | 62.9 |
| Net energy- lactation (Mcal/lb) | | 0.75 | 0.87 | 0.78 | 0.73 | 0.78 | 0.62 | 0.67 | 0.65 |
| Net energy- maint. (Mcal/lb) | | 0.74 | 0.86 | 0.77 | 0.72 | 0.77 | 0.59 | 0.65 | 0.62 |
| Net energy- gain (Mcal/lb) | | 0.48 | 0.58 | 0.51 | 0.46 | 0.51 | 0.35 | 0.37 | 0.35 |
| Digestible Energy (Mcal/lb) | | | | | | | | | |
| Metabolizable energy (Mcal/lb) | | | | | | | | | |
| Sulfur (%) | | 0.6 | 0.52 | 0.58 | 0.67 | 0.5 | 0.58 | 0.7 | 0.69 |
| Phosphorus (%) | | 0.3 | 0.29 | 0.41 | 0.34 | 0.32 | 0.36 | 0.4 | 0.35 |
| Potassium (%) | | 3.76 | 5.48 | 5.67 | 4.74 | 5.75 | 6.47 | 5.73 | 4.9 |
| Magnesium (%) | | 0.74 | 0.8 | 0.91 | 0.89 | 0.79 | 0.89 | 0.93 | 0.81 |
| Calcium (%) | | 1.99 | 1.69 | 2.01 | 2.19 | 1.82 | 1.85 | 2.1 | 2.01 |
| Sodium (%) | | 0.09 | 0.07 | 0.08 | 0.11 | 0.08 | 0.1 | 0.1 | 0.11 |
| Iron (ppm) | | 311 | 73 | 71 | 105 | 87 | 84 | 93 | 112 |
| Manganese (ppm) | | 39 | 24 | 25 | 25 | 23 | 20 | 25 | 20 |
| Copper (ppm) | | 11 | 9 | 9 | 7 | 7 | 8 | 8 | 7 |
| Zinc (ppm) | | 104 | 72 | 94 | 76 | 76 | 80 | 94 | 96 |
| Cobalt (ppm) | | 0.34 | 0.14 | 0.14 | 0.18 | 0.18 | 0.14 | 0.29 | 0.17 |

The next series of flats also includes the mixture of clovers, but planted at 5.2 grams/flat versus 2.6 grams/flat. The written and qualitative description given by the Fast & Fine Grass seed manufacturer was followed to establish the 2.6 and 5.2 grams seed/flat. In this series Flat 13 utilized the chelated minerals, cobalt, zinc, copper and manganese lactate planted at 50 grams/acre, which had the best response, about 200% of the control growth weight at cutting. These flats were harvested at 36 days of age, compared to 39 days of age in Flats 1-8. Flats had to be staged in harvesting as there was a lot of work getting them prepared for shipment. All harvested plants after cutting in the greenhouse were weighed first in the lab, frozen in zip lock bags then forwarded frozen to the lab for testing. Soils if to be sent to the lab were separated from plant roots, collected, placed in zip lock bags and sent immediately to the lab for testing The 50 grams/flat was chosen as a level because it matched pretty closely the per acre coverage of inorganic minerals presented with the Delt Ag product (for manganese and zinc). This demonstrates the power of the chelated cobalt when all other things are the same (13% ahead of that positive control).

Of interest in this series of flats was that Flat 13 apparently exhausted all the available phosphorus from the soil. The soil used for all flats was complete in nitrogen, phosphorus and potash and there was enough to last 3 to 4 months, but not for Flat 13.

TABLE 4

64 Flats, 2 Sq Ft/Flat
Miracle-Gro Garden Soil Composite
Each Flat, 0.25 CUFT soil Soil Analysis

| Flat Number | 1-56 | 17 | 18 | 19 | 20 | 21 | 22 | 23 | 24 |
|---|---|---|---|---|---|---|---|---|---|
| Seed Type | | Fast & Fine | Fast & Fine | Fast & Fine | Fast & Fine | Fast & Fine | Fast & Fine | Fast & Fine | Fast & Fine |
| Seed Planted (grams) | | 2.6 | 2.6 | 2.6 | 2.6 | 2.6 | 2.6 | 2.6 | 2.6 |
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 125 | 125 | 125 | 125 | 125 | 125 | 125 | 125 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | COBALT LACTATE MINERAL COMPLEX 2 |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |
| Solution (grams/mls H2O) Applied (solution in H2O) | | Water only Water (placebo) | 0.083/1000 10 ml in 600 | 0.882/1000 100 ml in 600 | 0.5/1000 100 ml in 600 | 0.23/1000 10 ml in 600 | 0.574/1000 10 ml in 600 | 0.5682/1000 100 ml in 600 | 0.574/1000 10 ml in 600 |
| 2nd Part (grams/mls H2O) Applied (solution in H2O) 2nd Part Description 2nd Part Chelated Minerals | | | | | | | | | 0.069/1000* 10 ml in 600 *3% min lactate Mn, Zn, Cu |
| Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | 5 |
| Organic zinc | | | | | | | | | 5 |
| Organic copper | | | | | | | | | 5 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 5 | 5 | 5 | 5 | 5 | 5 | 5 | 5 |
| Plant Harvest Date | | Aug. 29, 2009 | Aug. 29, 2009 | Aug. 29, 2009 | Aug. 29, 2009 | Aug. 29, 2009 | Aug. 29, 2009 | Aug. 29, 2009 | Aug. 29, 2009 |
| Age at Harvest (days) | | 49 | 49 | 49 | 49 | 49 | 49 | 49 | 49 |
| Weight (gms, as-is) | | 42.95 | 52.68 | 49.27 | 52.93 | 49.07 | 98.69 | 107.77 | 45.38 |
| % of Control | | 100 | 122.65 | 114.71 | 123.24 | 114.25 | 229.78 | 250.92 | 105.66 |
| Soil Analysis (dry weight) | | Submitted | Submitted | Submitted | Submitted | Submitted | Submitted | Submitted | Submitted |
| Moisture (%) | 52.91 | 44.94 | 57.58 | 54.17 | 58.75 | 52.92 | 52.5 | 54.61 | 53 |
| pH | 7.1 | 7.4 | 7.5 | 7.5 | 7.5 | 7.5 | 7.7 | 7.7 | 7.7 |
| Aerobic Plate Count (Mcfu/g) | 2.4 | 9.8 | 8.3 | 5.6 | 3.3 | 7.9 | 10.4 | 12.3 | 10.1 |
| Anaerobic Plate Count (Mcfu/g) | 0.1 | 0.36 | 0.39 | 0.26 | 0.12 | 0.29 | 0.3 | 0.49 | 0.71 |
| Azotobacter (Mcfu/g) | 3 | 3.6 | 5.2 | 4.6 | 3.2 | 1.6 | 26 | 10.2 | 5.8 |
| Microbial Activity (ug/10 g soil/day) | 245 | 1456 | 1771 | 1903 | 1926 | 1619 | 1692 | 1732 | 1556 |
| Total Nitrogen (N, %) | 1.13 | 1.04 | 1.32 | 1.11 | 1.36 | 1.08 | 1.26 | 1.17 | 1.15 |
| Ammonia Nitrogen (%) | 0 | 0 | nd | nd | nd | nd | nd | nd | nd |
| Nitrate Nitrogen (%) | nd | nd | nd | nd | nd | nd | nd | nd | nd |
| Organic Nitrogen (%) | 1.06 | 1.03 | 1.32 | 1.11 | 1.31 | 1.08 | 1.26 | 1.17 | 1.15 |
| Phosphorus (P2O5, %) | 0.23 | 0.25 | 0.33 | 0.35 | 0.34 | 0.34 | 0.34 | 0.31 | 0.3 |
| Potassium (K2O, %) | 0.25 | nd | nd | nd | nd | nd | nd | nd | nd |
| Sulfur (S, %) | 0.36 | 0.35 | 0.5 | 0.46 | 0.51 | 0.47 | 0.53 | 0.44 | 0.55 |
| Calcium (Ca, %) | 4.44 | 6.27 | 5.8 | 5.06 | 5.99 | 5.33 | 5.03 | 5.22 | 7.79 |
| Magnesium (Mg,%) | 1.83 | 2.74 | 2.31 | 1.7 | 2.3 | 2.08 | 1.73 | 1.96 | 3.49 |
| Sodium (Na, %) | 0.02 | 0.02 | 0.02 | nd | 0.02 | 0.02 | 0.02 | 0.02 | 0.02 |
| Copper (Cu, ppm) | nd | nd | nd | nd | nd | nd | nd | nd | nd |
| Iron (Fe, ppm) | 7539 | 7123 | 9974 | 8809 | 11576 | 10514 | 10322 | 9969 | 11702 |
| Manganese (Mn, ppm) | 200 | 232 | 264 | 253 | 272 | 268 | 288 | 251 | 353 |
| Zinc (Zn, ppm) | 65.8 | 70.8 | 103.7 | 87.3 | 106.7 | 99.8 | 113.7 | 94.7 | 106.4 |
| Total salts (per ton) | 3.61 | 5.54 | 4.01 | 3.61 | 3.99 | 4.01 | 3.82 | 3.8 | 5.85 |

TABLE 4-continued

64 Flats, 2 Sq Ft/Flat
Miracle-Gro Garden Soil Composite
Each Flat, 0.25 CUFT soil Soil Analysis

| Flat Number | 1-56 | 17 | 18 | 19 | 20 | 21 | 22 | 23 | 24 |
|---|---|---|---|---|---|---|---|---|---|
| Total Carbon (%) | 25.63 | 20.21 | 26.9 | 24.15 | 28.9 | 23.13 | 26.55 | 25.47 | 25.09 |
| C/N Ratio | 22.8:1 | 19.5:1 | 20.4:1 | 21.7:1 | 21.3:1 | 21.4:1 | 21:01 | 21.8:1 | 21.8:1 |
| Chloride | nd | nd | nd | nd | nd | nd | nd | nd | nd |
| Growth Media Extracts | | | | | | | | | |
| pH | 7.5 | 7.9 | 7.8 | 7.8 | 7.6 | 7.8 | 7.8 | 8 | 7.2 |
| Soluble salts (mS/cm) | 4.1 | 2.01 | 1.58 | 2.1 | 2.19 | 2.41 | 2.64 | 2.35 | 1.32 |
| Nitrate nitrogen (mg/L) | 246 | 1 | 0 | 0 | 0 | 5 | 2 | 0 | 0 |
| Phosphorus (P, mg/L) | 0.7 | 0.3 | 0.3 | 0.4 | 1 | 0.4 | 0.7 | 0.4 | 0.8 |
| Potassium (K, mg/L) | 294 | 43 | 59 | 44 | 47 | 57 | 70 | 40 | 47 |
| Calcium (Ca, mg/L) | 578 | 230 | 306 | 315 | 282 | 358 | 397 | 361 | 329 |
| Magnesium (mg, mg/L) | 210 | 89 | 118 | 120 | 110 | 138 | 156 | 138 | 127 |
| Sodium (Na, mg/L) | 91 | 33 | 48 | 36 | 36 | 42 | 62 | 43 | 38 |
| Plant Cuttings mixed forage (DW basis) | | | | | | | | | |
| Moisture (%) | | 77.64 | 77.9 | 77.09 | 75.85 | 75.27 | 76.99 | 77.16 | 74.4 |
| Dry Matter (%) | | 22.36 | 22.1 | 22.91 | 24.15 | 24.73 | 23.01 | 22.84 | 25.6 |
| Crude Protein (%) | | 12.4 | 12.8 | 11.7 | 10.6 | 9.6 | 11.1 | 12 | 10.7 |
| Crude Fat (%) | | 2.15 | 1.4 | 2.11 | 1.35 | 1.58 | 2.27 | 2.03 | 1.39 |
| Acid Detergent Fiber (%) | | 23 | 22.8 | 23.1 | 24.9 | 22.9 | 25.9 | 24.9 | 22.7 |
| Ash (%) | | 13.8 | 10.4 | 14.9 | 10.7 | 10.5 | 10.9 | 11.2 | 10.2 |
| Total digestible nutrients (%) | | 62 | 64.4 | 61.2 | 64.2 | 64.9 | 64 | 63.8 | 64.9 |
| Net energy- lactation (Mcal/lb) | | 0.8 | 0.8 | 0.8 | 0.78 | 0.8 | 0.76 | 0.78 | 0.8 |
| Net energy- maint. (Mcal/lb) | | 0.63 | 0.66 | 0.62 | 0.66 | 0.67 | 0.65 | 0.65 | 0.67 |
| Net energy- gain (Mcal/lb) | | 0.35 | 0.39 | 0.34 | 0.38 | 0.39 | 0.38 | 0.38 | 0.4 |
| Digestible Energy (Mcal/lb) | | 1.24 | 1.29 | 1.23 | 1.28 | 1.3 | 1.28 | 1.28 | 1.3 |
| Metabolizable energy (Mcal/lb) | | 1.16 | 1.2 | 1.15 | 1.2 | 1.22 | 1.2 | 1.19 | 1.22 |
| Sulfur (%) | | 0.35 | 0.37 | 0.32 | 0.35 | 0.31 | 0.34 | 0.46 | 0.36 |
| Phosphorus (%) | | 0.38 | 0.39 | 0.36 | 0.41 | 0.35 | 0.34 | 0.35 | 0.32 |
| Potassium (%) | | 3.45 | 3.5 | 3.32 | 2.9 | 2.73 | 3.19 | 3.43 | 2.77 |
| Magnesium (%) | | 0.44 | 0.44 | 0.45 | 0.43 | 0.38 | 0.4 | 0.49 | 0.41 |
| Calcium (%) | | 0.96 | 1.02 | 1.07 | 0.96 | 0.86 | 0.95 | 1.3 | 0.85 |
| Sodium (%) | | 0.06 | 0.07 | 0.06 | 0.05 | 0.05 | 0.06 | 0.07 | 0.06 |
| Iron (ppm) | | 61 | 58 | 55 | 56 | 72 | 63 | 79 | 54 |
| Manganese (ppm) | | 37 | 38 | 37 | 45 | 53 | 57 | 63 | 45 |
| Copper (ppm) | | 5 | 6 | 5 | 5 | 4 | 6 | 5 | 4 |
| Zinc (ppm) | | 89 | 91 | 92 | 80 | 79 | 94 | 122 | 73 |
| Cobalt (ppm) | | 6.6 | 4.1 | 3.5 | 3.7 | 3.5 | 5.92 | 5.43 | 1.1 |

The next series of flats, numbered 17 through 24 summarized in Table 4, contained the seeds used from the Fast & Fine Grass, noted in Table 1.

The results were the same with the cobalt lactate treated flats having the highest grass weights. Flats 23 and 22 had the best growth, over 200% of the control. Flat 23 was treated with 1238 grams/acre Cobalt Lactate Mineral Complex I and Flat 22 at 250 grams acre with Cobalt Lactate Mineral Complex I. Flat 23 was planted at exactly the same application rate of cobalt lactate as in 2008, 1 ppm based upon soil, and led the series at 251% of the control flat. Cobalt Lactate Mineral Complex I contains cobalt lactate, zinc sulfate, manganese sulfate, copper sulfate, *Yucca* extract, hemicellulose extract, Enzyme W, Porzyme and dextrose.

In those two flats the total aerobic plate count and *Azotobacter* count surged in numbers over all other treatments, the control and the baseline soil composite soil sample. It is clear in this series of flats that the relationship between soil microbes and growth is cause-and-effect; hence the support for the relationship between cobalt lactate and microbial populations that support plant growth. This is the second year now that 1 ppm cobalt lactate applied to the soil has resulted in double the grass growth.

The higher level of soil treatment minerals, at least in part, from the higher application rate of chelated minerals, cobalt, zinc, copper and manganese lactate in Flat 23 resulted in increased minerals being taken up by the grass in that flat. A look at the data shows that sulfur, magnesium, calcium, iron, manganese, zinc and cobalt were all higher or in the high-end range of plant mineral content for Flat 23 against all other treatments. The formulation includes chelated minerals, cobalt, zinc, copper and manganese lactate, hence the increased sulfur content (also important for plant growth), a small amount of *Yucca* extract, two enzymes and larch arabinogalactan. All of the combined effects may be adding to increased mineral transport from the soil to the plant, increasing available magnesium and calcium. Iron is also found in the cobalt carbonate raw material that is reacted with lactic acid to form cobalt lactate, hence the increased iron content, again, at least in part.

TABLE 5

64 Flats, 2 Sq Ft/Flat
Miracle-Gro Garden Soil Composite
Each Flat, 0.25 CUFT soil Soil Analysis

| Flat Number | 1-56 | 25 | 26 | 27 | 28 | 29 | 30 | 31 | 32 |
|---|---|---|---|---|---|---|---|---|---|
| Seed Type | | Food Plot Forage Mix | Food Plot Forage Mix | Food Plot Forage Mix | Food Plot Forage Mix | Food Plot Forage Mix | Food Plot Forage Mix | Food Plot Forage Mix | Food Plot Forage Mix |
| Seed Planted (grams) | | 5.2 | 5.2 | 5.2 | 5.2 | 5.2 | 5.2 | 5.2 | 5.2 |
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 249 | 249 | 249 | 249 | 249 | 249 | 249 | 249 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | COBALT LACTATE MINERAL COMPLEX 2 |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |
| Solution (grams/mls H2O) | | Water only | 0.083/1000 | 0.882/1000 | 0.5/1000 | 0.23/1000 | 0.574/1000 | 0.5682/1000 | 0.574/1000 |
| Applied (solution in H2O) | | Water (placebo) | 10 ml in 600 | 100 ml in 600 | 100 ml in 600 | 10 ml in 600 | 10 ml in 600 | 100 ml in 600 | 10 ml in 600 |
| 2nd Part (grams/mls H2O) | | | | | | | | | 0.069/1000* |
| Applied (solution in H2O) | | | | | | | | | 10 ml in 600 |
| 2nd Part Description | | | | | | | | | *3% min lactate |
| 2nd Part Chelated Minerals | | | | | | | | | Mn, Zn, Cu |
| Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | 5 |
| Organic zinc | | | | | | | | | 5 |
| Organic copper | | | | | | | | | 5 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 2 | 2 | 2 | 2 | 2 | 2 | 2 | 2 |
| Plant Harvest Date | | Aug. 12, 2009 | Aug. 23, 2009 | Aug. 23, 2009 | Aug. 23, 2009 | Aug. 23, 2009 | Aug. 23, 2009 | Aug. 23, 2009 | Aug. 23, 2009 |
| Age at Harvest (days) | | lost | 43 | 43 | 43 | 43 | 43 | 43 | 43 |
| Weight (gms, as-is) | | vandalism | 123.75 | 221.03 | 512.46 | 448.78 | 428.12 | 389.88 | 189.51 |
| % of Control | | | 100 | 178.61 | 414.11 | 362.65 | 345.96 | 315.05 | 153.14 |
| Soil Analysis (dry weight) | | Not submitted | Not submitted | Not submitted | Not submitted | Not submitted | Not submitted | Not submitted | Not submitted |
| Moisture (%) | 52.91 | | | | | | | | |
| pH | 7.1 | | | | | | | | |
| Aerobic Plate Count (Mcfu/g) | 2.4 | | | | | | | | |
| Anaerobic Plate Count (Mcfu/g) | 0.1 | | | | | | | | |
| Azotobacter (Mcfu/g) | 3 | | | | | | | | |
| Microbial Activity (ug/10 g soil/day) | 245 | | | | | | | | |
| Total Nitrogen (N, %) | 1.13 | | | | | | | | |
| Ammonia Nitrogen (%) | 0 | | | | | | | | |
| Nitrate Nitrogen (%) | nd | | | | | | | | |
| Organic Nitrogen (%) | 1.06 | | | | | | | | |
| Phosphorus (P2O5, %) | 0.23 | | | | | | | | |
| Potassium (K2O, %) | 0.25 | | | | | | | | |
| Sulfur (S, %) | 0.36 | | | | | | | | |
| Calcium (Ca, %) | 4.44 | | | | | | | | |
| Magnesium (Mg, %) | 1.83 | | | | | | | | |
| Sodium (Na, %) | 0.02 | | | | | | | | |
| Copper (Cu, ppm) | nd | | | | | | | | |
| Iron (Fe, ppm) | 7539 | | | | | | | | |
| Manganese (Mn, ppm) | 200 | | | | | | | | |

TABLE 5-continued

64 Flats, 2 Sq Ft/Flat
Miracle-Gro Garden Soil Composite
Each Flat, 0.25 CUFT soil Soil Analysis

| Flat Number | 1-56 | 25 | 26 | 27 | 28 | 29 | 30 | 31 | 32 |
|---|---|---|---|---|---|---|---|---|---|
| Zinc (Zn, ppm) | 65.8 | | | | | | | | |
| Total salts (per ton) | 3.61 | | | | | | | | |
| Total Carbon (%) | 25.63 | | | | | | | | |
| C/N Ratio | 22.8:1 | | | | | | | | |
| Chloride | nd | | | | | | | | |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |
| Plant Cuttings mixed forage (DW basis) | | Vandalized | | | | | | | |
| Moisture (%) | | | 78.97 | 79.11 | 83.75 | 84.94 | 84.38 | 84.64 | 82.41 |
| Dry Matter (%) | | | 21.03 | 20.89 | 16.25 | 15.06 | 15.62 | 15.54 | 17.59 |
| Crude Protein (%) | | | 8.39 | 8.1 | 8.57 | 8.34 | 9.21 | 8.93 | 9.69 |
| Crude Fat (%) | | | 2.28 | 2.36 | 3.42 | 3.21 | 2.64 | 2.4 | 2.5 |
| Acid Detergent Fiber (%) | | | 16.3 | 17.8 | 21.6 | 20.1 | 18.9 | 22.7 | 26.3 |
| Ash (%) | | | 11.9 | 13 | 11.9 | 13.1 | 13 | 12.9 | 13.7 |
| Total digestible nutrients (%) | | | 65 | 64 | 64.4 | 63.7 | 63.7 | 63.2 | 61.9 |
| Net energy-lactation (Mcal/lb) | | | 0.88 | 0.86 | 0.81 | 0.83 | 0.85 | 0.8 | 0.75 |
| Net energy- maint. (Mcal/lb) | | | 0.67 | 0.65 | 0.66 | 0.65 | 0.65 | 0.64 | 0.63 |
| Net energy- gain (Mcal/lb) | | | 0.4 | 0.38 | 0.39 | 0.38 | 0.38 | 0.37 | 0.35 |
| Digestible Energy (Mcal/lb) | | | 1.3 | 1.28 | 1.29 | 1.27 | 1.27 | 1.26 | 1.24 |
| Metabolizable energy (Mcal/lb) | | | 1.23 | 1.21 | 1.21 | 1.2 | 1.2 | 1.19 | 1.16 |
| Sulfur (%) | | | 1.13 | 1.03 | 0.88 | 0.92 | 0.92 | 0.83 | 1.04 |
| Phosphorus (%) | | | 0.38 | 0.28 | 0.35 | 0.35 | 0.38 | 0.36 | 0.4 |
| Potassium (%) | | | 2.14 | 2.18 | 2.91 | 2.92 | 3.02 | 2.89 | 3.02 |
| Magnesium (%) | | | 0.68 | 0.67 | 0.57 | 0.62 | 0.6 | 0.56 | 0.68 |
| Calcium (%) | | | 2.89 | 2.89 | 2.9 | 3.07 | 2.86 | 2.84 | 3.15 |
| Sodium (%) | | | 0.13 | 0.17 | 0.08 | 0.1 | 0.09 | 0.09 | 0.12 |
| Iron (ppm) | | | 42 | 36 | 80 | 43 | 43 | 52 | 56 |
| Manganese (ppm) | | | 20 | 20 | 27 | 27 | 30 | 33 | 22 |
| Copper (ppm) | | | 3 | 2 | 2 | 2 | 3 | 2 | 3 |
| Zinc (ppm) | | | 65 | 80 | 93 | 110 | 88 | 93 | 93 |
| Cobalt (ppm) | | | 3.12 | 5.9 | 4.35 | 4.67 | 4.3 | 2.75 | 4.08 |

Flats 25-32 are those in the next series, which include a combination of seeds that includes Green Globe Turnips, Dwarf Essex Forage Rapeseed, Rangi Forage and Giant Rapeseed. They are largely sold to land owners to support wild life.

The best performances in this series of flats were numbers 28, 29 and 30, respectively. Flat 26 treated with Delt Ag was used as the control. With that in mind, flats 28, 29 and 30 were about 300 to 400% of the control and looked pretty remarkable compared to it.

Flats 29 and 30 were treated with chelated minerals, cobalt, zinc, copper and manganese lactate at 50 and 125 grams/acre, respectively. However, the best flat in the series was treated with a *Yucca* extract. The literature on *Yucca* and improved plant performance relates to soil treatment and improved permeability of plant cells to growth media in the soil. Of the seven series of flats that were treated with *Yucca* extract and the chelated minerals, cobalt, zinc, copper and manganese lactate, *Yucca* performed best in two of those series.

TABLE 6

64 Flats, 2 Sq Ft/Flat
Miracle-Gro Garden Soil Composite
Each Flat, 0.25 CUFT soil Soil Analysis

| Flat Number | 1-56 | 33 | 34 | 35 | 36 | 37 | 38 | 39 | 40 |
|---|---|---|---|---|---|---|---|---|---|
| Seed Type | | Food Plot Grain Mix | Food Plot Grain Mix | Food Plot Grain Mix | Food Plot Grain Mix | Food Plot Grain Mix | Food Plot Grain Mix | Food Plot Grain Mix | Food Plot Grain Mix |
| Seed Planted (grams) | | 5.2 | 5.2 | 5.2 | 5.2 | 5.2 | 5.2 | 5.2 | 5.2 |

TABLE 6-continued

64 Flats, 2 Sq Ft/Flat
Miracle-Gro Garden Soil Composite
Each Flat, 0.25 CUFT soil Soil Analysis

| Flat Number | 1-56 | 33 | 34 | 35 | 36 | 37 | 38 | 39 | 40 |
|---|---|---|---|---|---|---|---|---|---|
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 249 | 249 | 249 | 249 | 249 | 249 | 249 | 249 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | COBALT LACTATE MINERAL COMPLEX 2 |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |
| Solution (grams/mls H2O) Applied (solution in H2O) | | Water only Water (placebo) | 0.083/1000 10 ml in 600 | 0.882/1000 100 ml in 600 | 0.5/1000 100 ml in 600 | 0.23/1000 10 ml in 600 | 0.574/1000 10 ml in 600 | 0.5682/1000 100 ml in 600 | 0.574/1000 10 ml in 600 |
| 2nd Part (grams/mls H2O) Applied (solution in H2O) 2nd Part Description | | | | | | | | | 0.069/1000* 10 ml in 600 *3% min lactate Mn, Zn, Cu |
| 2nd Part Chelated Minerals Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | 5 |
| Organic zinc | | | | | | | | | 5 |
| Organic copper | | | | | | | | | 5 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 2 | 2 | 2 | 2 | 2 | 2 | 2 | 2 |
| Plant Harvest Date | | Aug. 15, 2009 | Aug. 15, 2009 | Aug. 15, 2009 | Aug. 15, 2009 | Aug. 15, 2009 | Aug. 12, 2009 | Aug. 12, 2009 | Aug. 12, 2009 |
| Age at Harvest (days) | | 35 | 35 | 35 | 35 | 35 | lost | lost | lost |
| Weight (gms, as-is) | | 426.28 | 442.08 | 355.57 | 353.26 | 492.63 | vandalism | vandalism | vandalism |
| % of Control | | 100 | 103.71 | 83.41 | 82.87 | 115.56 | | | |
| Soil Analysis (dry weight) | | Submitted | Submitted | Submitted | Submitted | Submitted | N/A | N/A | N/A |
| Moisture (%) | 52.91 | 64.27 | 54.48 | 62.92 | 58.91 | 60.35 | | | |
| pH | 7.1 | 7.6 | 7.6 | 7.5 | 7.5 | 7.5 | | | |
| Aerobic Plate Count (Mcfu/g) | 2.4 | 19 | 25 | 21 | 13 | 5 | | | |
| Anaerobic Plate Count (Mcfu/g) | 0.1 | 0.83 | 0.73 | 0.53 | 0.7 | 0.91 | | | |
| Azotobacter (Mcfu/g) | 3 | 60 | 111 | 37 | 55 | 61 | | | |
| Microbial Activity (ug/10 g soil/day) | 245 | 2255 | 2287 | 2216 | 2021 | 2069 | | | |
| Total Nitrogen (N, %) | 1.13 | 1.23 | 1.19 | 1.32 | 1.34 | 1.21 | | | |
| Ammonia Nitrogen (%) | 0 | 0.01 | 0 | nd | nd | 0 | | | |
| Nitrate Nitrogen (%) | nd | nd | nd | nd | nd | nd | | | |
| Organic Nitrogen (%) | 1.06 | 1.23 | 1.18 | 1.32 | 1.34 | 1.21 | | | |
| Phosphorus (P2O5, %) | 0.23 | 0.31 | 0.24 | 0.3 | 0.27 | nd | | | |
| Potassium (K2O, %) | 0.25 | nd | nd | nd | nd | nd | | | |
| Sulfur (S, %) | 0.36 | 0.45 | 0.37 | 0.51 | 0.44 | 0.48 | | | |
| Calcium (Ca, %) | 4.44 | 4.42 | 3.67 | 7.04 | 4.33 | 9.96 | | | |
| Magnesium (Mg, %) | 1.83 | 1.68 | 1.32 | 3.18 | 1.53 | 3.98 | | | |
| Sodium (Na, %) | 0.02 | 0.03 | 0.02 | 0.16 | 0.05 | 0.05 | | | |
| Copper (Cu, ppm) | nd | nd | nd | nd | nd | nd | | | |
| Iron (Fe, ppm) | 7539 | 8741 | 7377 | 8862 | 8866 | 8971 | | | |
| Manganese (Mn, ppm) | 200 | 227 | 209 | 243 | 221 | 245 | | | |
| Zinc (Zn, ppm) | 65.8 | 98 | 96.7 | 94.4 | 94.9 | 90.8 | | | |
| Total salts (per ton) | 3.61 | 2.63 | 2.82 | 4.34 | 2.98 | 6.03 | | | |

TABLE 6-continued

64 Flats, 2 Sq Ft/Flat
Miracle-Gro Garden Soil Composite
Each Flat, 0.25 CUFT soil Soil Analysis

| Flat Number | 1-56 | 33 | 34 | 35 | 36 | 37 | 38 | 39 | 40 |
|---|---|---|---|---|---|---|---|---|---|
| Total Carbon (%) | 25.63 | 26.14 | 24.63 | 26.86 | 27.77 | 25.3 | | | |
| C/N Ratio | 22.8:1 | 21.2:1 | 20.8:1 | 20.3:1 | 20.7:1 | 20.9:1 | | | |
| Chloride | nd | nd | nd | nd | nd | nd | | | |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |
| Plant Cuttings mixed forage (DW basis) | | | | | | | Vandalism | Vandalism | Vandalism |
| Moisture (%) | | 84.7 | 84.01 | 83.35 | 84.67 | 83.6 | | | |
| Dry Matter (%) | | 15.3 | 15.99 | 16.65 | 15.33 | 16.4 | | | |
| Crude Protein (%) | | 6.96 | 5.81 | 7.14 | 6.39 | 7.08 | | | |
| Crude Fat (%) | | | | | | | | | |
| Acid Detergent Fiber (%) | | 34.4 | 33.8 | 29.5 | 36.8 | 30.4 | | | |
| Ash (%) | | | | | | | | | |
| Total digestible nutrients (%) | | 63.3 | 64 | 68.9 | 60.6 | 67.9 | | | |
| Net energy-lactation (Mcal/lb) | | 0.65 | 0.66 | 0.71 | 0.62 | 0.7 | | | |
| Net energy- maint. (Mcal/lb) | | 0.63 | 0.64 | 0.7 | 0.6 | 0.68 | | | |
| Net energy- gain (Mcal/lb) | | 0.35 | 0.36 | 0.43 | 0.36 | 0.42 | | | |
| Digestible Energy (Mcal/lb) | | | | | | | | | |
| Metabolizable energy (Mcal/lb) | | | | | | | | | |
| Sulfur (%) | | | 0.39 | 0.29 | 0.33 | 0.3 | 0.28 | | |
| Phosphorus (%) | | 0.25 | 0.23 | 0.25 | 0.24 | 0.19 | | | |
| Potassium (%) | | 3.43 | 3.14 | 3.38 | 3.25 | 3.07 | | | |
| Magnesium (%) | | 0.55 | 0.47 | 0.48 | 0.43 | 0.47 | | | |
| Calcium (%) | | 1.11 | 0.88 | 0.87 | 0.86 | 0.89 | | | |
| Sodium (%) | | 0.05 | 0.03 | 0.04 | 0.03 | 0.03 | | | |
| Iron (ppm) | | 101 | 61 | 54 | 35 | 56 | | | |
| Manganese (ppm) | | 20 | 15 | 9 | 6 | 9 | | | |
| Copper (ppm) | | 13 | 8 | 4 | 3 | 3 | | | |
| Zinc (ppm) | | 50 | 39 | 42 | 34 | 36 | | | |
| Cobalt (ppm) | | 0.9 | 0.29 | 0.27 | 0.15 | 0.2 | | | |

The next series of flats includes the Food Plot Grain Mix, a combination of seeds for game as described earlier. The plants were over three feet tall. The chelated minerals, cobalt, zinc, copper and manganese lactate at 50 grams per acre was significantly ahead of all the other treatments and control.

TABLE 7

64 Flats, 2 Sq Ft/Flat
Miracle-Gro Garden Soil Composite
Each Flat, 0.25 CUFT soil Soil Analysis

| Flat Number | 1-56 | 41 | 42 | 43 | 44 | 45 | 46 | 47 | 48 |
|---|---|---|---|---|---|---|---|---|---|
| Seed Type | | Alfalfa (Vernal) | Alfalfa (Vernal) | Alfalfa (Vernal) | Alfalfa (Vernal) | Alfalfa (Vernal) | Alfalfa (Vernal) | Alfalfa (Vernal) | Alfalfa (Vernal) |
| Seed Planted (grams) | | 5.2 | 5.2 | 5.2 | 5.2 | 5.2 | 5.2 | 5.2 | 5.2 |
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 249 | 249 | 249 | 249 | 249 | 249 | 249 | 249 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |

TABLE 7-continued

64 Flats, 2 Sq Ft/Flat
Miracle-Gro Garden Soil Composite
Each Flat, 0.25 CUFT soil Soil Analysis

| Flat Number | 1-56 | 41 | 42 | 43 | 44 | 45 | 46 | 47 | 48 |
|---|---|---|---|---|---|---|---|---|---|
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | COBALT LACTATE MINERAL COMPLEX 2 |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |
| Solution (grams/mls H2O) | | Water only | 0.083/1000 | 0.882/1000 | 0.5/1000 | 0.23/1000 | 0.574/1000 | 0.5682/1000 | 0.574/1000 |
| Applied (solution in H2O) | | Water (placebo) | 10 ml in 600 | 100 ml in 600 | 100 ml in 600 | 10 ml in 600 | 10 ml in 600 | 100 ml in 600 | 10 ml in 600 |
| 2nd Part (grams/mls H2O) | | | | | | | | | 0.069/1000* |
| Applied (solution in H2O) | | | | | | | | | 10 ml in 600 |
| 2nd Part Description | | | | | | | | | *3% min lactate |
| 2nd Part Chelated Minerals | | | | | | | | | Mn, Zn, Cu |
| Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | 5 |
| Organic zinc | | | | | | | | | 5 |
| Organic copper | | | | | | | | | 5 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 1 | 1 | 1 | 1 | 1 | 1 | 1 | 1 |
| Plant Harvest Date | | Aug. 25, 2009 | Aug. 25, 2009 | Aug. 25, 2009 | Aug. 25, 2009 | Aug. 25, 2009 | Aug. 25, 2009 | Aug. 25, 2009 | Aug. 25, 2009 |
| Age at Harvest (days) | | 45 | 45 | 45 | 45 | 45 | 45 | 45 | 45 |
| Weight (gms, as-is) | | 198.02 | 198.85 | 231.52 | 205.83 | 227.66 | 209.69 | 263.44 | 185.64 |
| % of Control | | 100 | 100.42 | 116.92 | 103.94 | 114.97 | 105.89 | 133.04 | 93.75 |
| Soil Analysis (dry weight) | | Submitted | Submitted | Submitted | Submitted | Submitted | Submitted | Submitted | Submitted |
| Moisture (%) | 52.91 | 43.14 | 49.94 | 47.12 | 48.71 | 47.35 | 46.91 | 50.51 | 53.48 |
| pH | 7.1 | 7.5 | 7.7 | 7.6 | 7.6 | 7.7 | 7.6 | 7.6 | 7.6 |
| Aerobic Plate Count (Mcfu/g) | 2.4 | 1.3 | 4.4 | 2.1 | 4 | 3.3 | 2.2 | 2.1 | 2 |
| Anaerobic Plate Count (Mcfu/g) | 0.1 | 0.15 | 0.24 | 0.07 | 0.074 | 0.082 | 0.21 | 0.07 | 0.042 |
| Azotobacter (Mcfu/g) | 3 | 33 | 55 | 33 | 43 | 12 | 9 | 29 | 26 |
| Microbial Activity (ug/10 g soil/day) | 245 | 1891 | 2264 | 2149 | 2029 | 1995 | 1169 | 2387 | 2011 |
| Total Nitrogen (N, %) | 1.13 | 1.23 | 1.44 | 1.44 | 1.52 | 1.52 | 1.49 | 1.33 | 1.53 |
| Ammonia Nitrogen (%) | 0 | nd | nd | nd | nd | nd | nd | nd | nd |
| Nitrate Nitrogen (%) | nd | nd | nd | nd | nd | nd | nd | nd | nd |
| Organic Nitrogen (%) | 1.06 | 1.23 | 1.44 | 1.44 | 1.52 | 1.52 | 1.49 | 1.33 | 1.53 |
| Phosphorus (P2O5, %) | 0.23 | 0.23 | 0.22 | 0.25 | 0.27 | 0.32 | 0.26 | 0.32 | 0.28 |
| Potassium (K2O, %) | 0.25 | nd | nd | nd | nd | nd | nd | nd | nd |
| Sulfur (S, %) | 0.36 | 0.37 | 0.36 | 0.36 | 0.37 | 0.46 | 0.4 | 0.4 | 0.37 |
| Calcium (Ca, %) | 4.44 | 3.78 | 3.74 | 4.65 | 4.82 | 4.5 | 4.86 | 4.73 | 4.39 |
| Magnesium (Mg, %) | 1.83 | 1.42 | 1.32 | 1.93 | 1.93 | 1.67 | 1.88 | 1.82 | 1.68 |
| Sodium (Na, %) | 0.02 | nd | nd | 0.02 | nd | 0.02 | nd | nd | nd |
| Copper (Cu, ppm) | nd | nd | nd | nd | nd | nd | nd | nd | nd |
| Iron (Fe, ppm) | 7539 | 7355 | 7697 | 7685 | 9503 | 9299 | 8574 | 9028 | 7556 |
| Manganese (Mn, ppm) | 200 | 190 | 208 | 216 | 238 | 281 | 220 | 238 | 211 |
| Zinc (Zn, ppm) | 65.8 | 77.4 | 89.9 | 83.2 | 105.3 | 106.4 | 92.3 | 123.3 | 101 |
| Total salts (per ton) | 3.61 | 3.67 | 3.26 | 4.25 | 4.25 | 4.06 | 4.38 | 3.91 | 3.54 |
| Total Carbon (%) | 25.63 | 23.21 | 26.07 | 25.51 | 26.73 | 25.38 | 27.93 | 25.94 | 28.31 |
| C/N Ratio | 22.8:1 | 18.9:1 | 18.1:1 | 17.8:1 | 17.6:1 | 16.7:1 | 18.8:1 | 19.5:1 | 18.5:1 |
| Chloride | nd | nd | nd | nd | nd | nd | nd | nd | nd |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |

TABLE 7-continued

64 Flats, 2 Sq Ft/Flat
Miracle-Gro Garden Soil Composite
Each Flat, 0.25 CUFT soil Soil Analysis

| Flat Number | 1-56 | 41 | 42 | 43 | 44 | 45 | 46 | 47 | 48 |
|---|---|---|---|---|---|---|---|---|---|
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |
| Plant Cuttings mixed forage (DW basis) | | | | | | | | | |
| Moisture (%) | | 79.76 | 76.07 | 80.24 | 80.83 | 80.07 | 78.91 | 81.08 | 83 |
| Dry Matter (%) | | 20.24 | 23.93 | 19.76 | 19.17 | 19.93 | 21.09 | 18.92 | 17 |
| Crude Protein (%) | | 22.2 | 20.4 | 21.5 | 21.7 | 17.8 | 16.2 | 17 | 23.4 |
| Crude Fat (%) | | 1.67 | 1.7 | 1.67 | 1.69 | 2.2 | 1.48 | 1.11 | 1.76 |
| Acid Detergent Fiber (%) | | 39.6 | 38.7 | 38.8 | 31.4 | 32.6 | 34.8 | 48.7 | 25.4 |
| Ash (%) | | 12.2 | 10.8 | 11.1 | 12.1 | 12.1 | 11.2 | 11.8 | 13.4 |
| Total digestible nutrients (%) | | 64.2 | 65.5 | 65.2 | 65 | 65.1 | 65.7 | 64.1 | 64.4 |
| Net energy-lactation (Mcal/lb) | | 0.57 | 0.58 | 0.58 | 0.67 | 0.66 | 0.63 | 0.46 | 0.74 |
| Net energy- maint. (Mcal/lb) | | 0.66 | 0.67 | 0.67 | 0.67 | 0.67 | 0.68 | 0.65 | 0.66 |
| Net energy- gain (Mcal/lb) | | 0.39 | 0.4 | 0.4 | 0.4 | 0.4 | 0.41 | 0.38 | 0.39 |
| Digestible Energy (Mcal/lb) | | 1.28 | 1.31 | 1.3 | 1.3 | 1.3 | 1.31 | 1.28 | 1.29 |
| Metabolizable energy (Mcal/lb) | | 1.18 | 1.2 | 1.2 | 1.19 | 1.2 | 1.22 | 1.19 | 1.18 |
| Sulfur (%) | | 0.42 | 0.52 | 0.53 | 0.59 | 0.66 | 0.49 | 0.47 | 0.62 |
| Phosphorus (%) | | 0.26 | 0.25 | 0.26 | 0.33 | 0.32 | 0.24 | 0.26 | 0.34 |
| Potassium (%) | | 3.21 | 3.28 | 3.67 | 4.46 | 4.53 | 3.7 | 3.91 | 4.58 |
| Magnesium (%) | | 0.37 | 0.49 | 0.49 | 0.49 | 0.55 | 0.44 | 0.43 | 0.51 |
| Calcium (%) | | 1.48 | 2 | 2 | 2.06 | 2.2 | 1.74 | 1.67 | 2.05 |
| Sodium (%) | | 0.05 | 0.06 | 0.07 | 0.07 | 0.08 | 0.06 | 0.07 | 0.07 |
| Iron (ppm) | | 65 | 64 | 67 | 86 | 96 | 62 | 84 | 107 |
| Manganese (ppm) | | 22 | 28 | 28 | 29 | 27 | 23 | 24 | 35 |
| Copper (ppm) | | 4 | 4 | 4 | 4 | 5 | 4 | 4 | 5 |
| Zinc (ppm) | | 49 | 49 | 60 | 63 | 71 | 54 | 64 | 66 |
| Cobalt (ppm) | | 0.45 | 0.28 | 0.16 | 0.23 | 0.26 | 0.18 | 0.21 | 0.47 |

This series of flats is the first of two planted with alfalfa. A Vernal variety was chosen because it was reported that this variety is accepted across the industry as a greenhouse standard.

As seen in Table 7, treatments followed the same pattern as in all of the preceding series of flats. The best response in this series was form Flat 47, the seed treated with the highest level of the chelated minerals, cobalt, zinc, copper and manganese lactate, at 1238 grams/acre. Growth at 133% of the control was significantly above any other treatment response. Nonetheless, the best response in this seemingly optimized alfalfa seed was with the chelated minerals, cobalt, zinc, copper and manganese lactate.

TABLE 8

64 Flats, 2 Sq Ft/Flat
Miracle-Gro Garden Soil Composite
Each Flat, 0.25 CUFT soil Soil Analysis

| Flat Number | 1-56 | 49 | 50 | 51 | 52 | 53 | 54 | 55 | 56 |
|---|---|---|---|---|---|---|---|---|---|
| Seed Type | | Alfalfa (Vernal) | Alfalfa (Vernal) | Alfalfa (Vernal) | Alfalfa (Vernal) | Alfalfa (Vernal) | Alfalfa (Vernal) | Alfalfa (Vernal) | Alfalfa (Vernal) |
| Seed Planted (grams) | | 2.6 | 2.6 | 2.6 | 2.6 | 2.6 | 2.6 | 2.6 | 2.6 |
| Seed Planted (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Seeding Rate (#/acre) | | 125 | 125 | 125 | 125 | 125 | 125 | 125 | 125 |
| Soil Treated (date) | | Jul. 11, 2009 | Jul. 11, 2009 | Jul. 11, 2009 | Jul. 11, 2009 | Jul. 11, 2009 | Jul. 11, 2009 | Jul. 11, 2009 | Jul. 11, 2009 |
| Soil Treated (with) | | Nothing | Delt Ag S. Coat | Plot Max | Yucca | Cobalt Lactate Mineral Complex 1 | Cobalt Lactate Mineral Complex 1 | Cobalt Lactate Mineral Complex 1 | FP250X |
| Treatment (grams per acre) | | Nothing | 18 | 1920 | 1529 | 50 | 125 | 1238 | 140 |
| DM Treat (grams/acre) | | Nothing | 18 | 58 | 535 | 50 | 125 | 1238 | 140 |

TABLE 8-continued

64 Flats, 2 Sq Ft/Flat
Miracle-Gro Garden Soil Composite
Each Flat, 0.25 CUFT soil Soil Analysis

| Flat Number | 1-56 | 49 | 50 | 51 | 52 | 53 | 54 | 55 | 56 |
|---|---|---|---|---|---|---|---|---|---|
| Solution (grams/mls H2O) | Water only | | 0.083/1000 | 0.882/1000 | 0.5/1000 | 0.23/1000 | 0.574/1000 | 0.5682/1000 | 0.574/1000 |
| Applied (solution in H2O) | Water (placebo) | 10 ml in 600 | 100 ml in 600 | 100 ml in 600 | 10 ml in 600 | 10 ml in 600 | 100 ml in 600 | 10 ml in 600 |
| 2nd Part (grams/mls H2O) | | | | | | | | | 0.069/1000* |
| Applied (solution in H2O) | | | | | | | | | 10 ml in 600 |
| 2nd Part Description | | | | | | | | | *3% min lactate |
| 2nd Part Chelated Minerals | | | | | | | | | Mn, Zn, Cu |
| Mineral Application, gm/acre | | | | | | | | | |
| Organic cobalt | | | | | | 2.2 | 5.5 | 54.5 | 5.5 |
| Manganese | | | 0.46 | | | 0.43 | 1.08 | 10.7 | 1.08 |
| Zinc | | | 0.53 | | | 0.49 | 1.23 | 12.2 | 1.23 |
| Copper | | | | | | 0.48 | 1.2 | 11.9 | 1.2 |
| Organic manganese | | | | | | | | | |
| Oganic zinc | | | | | | | | | |
| Organic copper | | | | | | | | | |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 1 | 1 | 1 | 1 | 1 | 1 | 1 | 1 |
| Plant Harvest Date | | Sep. 27, 2009 | Sep. 27, 2009 | Sep. 27, 2009 | Sep. 27, 2009 | Sep. 27, 2009 | Sep. 27, 2009 | Sep. 27, 2009 | Sep. 27, 2009 |
| Age at Harvest (days) | | 78 | 78 | 78 | 78 | 78 | 78 | 78 | 78 |
| Weight (gms, as-is) | | 318.86 | 311.61 | 301.77 | 323.46 | 248.36 | 249.64 | 221.66 | 222.11 |
| % of Control | | 100 | 97.73 | 94.64 | 101.44 | 77.89 | 78.29 | 69.52 | 69.66 |
| Soil Analysis (dry weight) | | | | | | | | | |
| Moisture (%) | 52.91 | | | | | | | | |
| pH | 7.1 | | | | | | | | |
| Aerobic Plate Count (Mcfu/g) | 2.4 | | | | | | | | |
| Anaerobic Plate Count (Mcfu/g) | 0.1 | | | | | | | | |
| Azotobacter (Mcfu/g) | 3 | | | | | | | | |
| Microbial Activity (ug/10 g soil/day) | 245 | | | | | | | | |
| Total Nitrogen (N, %) | 1.13 | | | | | | | | |
| Ammonia Nitrogen (%) | 0 | | | | | | | | |
| Nitrate Nitrogen (%) | nd | | | | | | | | |
| Organic Nitrogen (%) | 1.06 | | | | | | | | |
| Phosphorus (P2O5, %) | 0.23 | | | | | | | | |
| Potassium (K2O, %) | 0.25 | | | | | | | | |
| Sulfur (S, %) | 0.36 | | | | | | | | |
| Calcium (Ca, %) | 4.44 | | | | | | | | |
| Magnesium (Mg, %) | 1.83 | | | | | | | | |
| Sodium (Na, %) | 0.02 | | | | | | | | |
| Copper (Cu, ppm) | nd | | | | | | | | |
| Iron (Fe, ppm) | 7539 | | | | | | | | |
| Manganese (Mn, ppm) | 200 | | | | | | | | |
| Zinc (Zn, ppm) | 65.8 | | | | | | | | |
| Total salts (per ton) | 3.61 | | | | | | | | |
| Total Carbon (%) | 25.63 | | | | | | | | |
| C/N Ratio | 22.8:1 | | | | | | | | |
| Chloride | nd | | | | | | | | |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |

The next series is the second Vernal alfalfa set, this time planted at 2.6 grams/flat versus the previous section at 5.6 grams/flat. The most notable characteristic of this series is that all flats except Flat 52, treated with the *Yucca* extract, performed worse than the control. The seeding rate was low enough that the treatments (except for *Yucca*) were too much to increase growth and instead inhibited plant development.

TABLE 9

64 Flats, 2 Sq Ft/Flat
Miracle-Gro Garden Soil Composite
Each Flat, 0.25 CUFT soil Soil Analysis

| Flat Number | 1-56 | 57 | 58 | 59 | 60 | 61 | 62 | 63 | 64 |
|---|---|---|---|---|---|---|---|---|---|
| Seed Type | | Food Plot Clover Mix | Food Plot Clover Mix | Food Plot Clover Mix | Food Plot Clover Mix | Food Plot Clover Mix | Food Plot Clover Mix | Food Plot Clover Mix | Food Plot Clover Mix |
| Seed Planted (grams) | | 5.2 | 5.2 | 5.2 | 5.2 | 5.2 | 5.2 | 5.2 | 5.2 |
| Seed Planted (date) | | Jul. 12, 2009 | Jul. 12, 2009 | Jul. 12, 2009 | Jul. 12, 2009 | Jul. 12, 2009 | Jul. 12, 2009 | Jul. 12, 2009 | Jul. 12, 2009 |
| Seeding Rate (#/acre) | | 249 | 249 | 249 | 249 | 249 | 249 | 249 | 249 |
| Soil Treated (date) | | Jul. 12, 2009 | Jul. 12, 2009 | Jul. 12, 2009 | Jul. 12, 2009 | Jul. 12, 2009 | Jul. 12, 2009 | Jul. 12, 2009 | Jul. 12, 2009 |
| Soil Treated (with) | | Nothing | Colorburst | Colorburst | Cobalt Lactate Mineral Complex 1 | 125 + Chelated | BK Chelated | BK Chelated | BK Chelated |
| Treatment (grams per acre) | | Nothing | 10890000 | 21780000 | 2476 | 1586 | 8712 | 17424 | 26136 |
| DM Treat (grams/acre) | | Nothing | 32670 | 65340 | 2476 | 1586 | 348 | 696 | 1045 |
| Solution (grams/mls H2O) | | Water only | 12/4000 | 12/4000 | 0.5682/1000 | 0.5682/1000 | 0.4/100 | 0.8/100 | 1.2/100 |
| Applied (solution in H2O) | | Water | 500 ml | 1000 ml | 200 ml in 600 | 100 ml in 600 | 100 ml in 600 | 100 ml in 600 | 100 ml in 600 |
| 2nd Part (grams/mls H2O) Applied (solution in H2O) | | | | | | 0.4 gm neat | | | |
| 2nd Part Description | | | | | | 4% min lactate | 4% min lactate | 4% min lactate | 4% min lactate |
| 2nd Part Chelated Minerals | | | | | | Co, Mn, Zn, Cu | Co, Mn, Zn, Cu | Co, Mn, Zn, Cu | Co, Mn, Zn, Cu |
| Mineral Application, gm/acre | | | | | | | | | |
| Organic cobalt | | | | | 109 | 5.5 | 21.8 | 43.6 | 65.4 |
| Manganese | | | | | 21.4 | 1.08 | | | |
| Zinc | | | 19.6 | 39.2 | 24.4 | 1.23 | | | |
| Copper | | | 22.8 | 45.6 | 23.8 | 1.2 | | | |
| Organic manganese | | | 16.3 | 32.6 | | 21.8 | 21.8 | 43.6 | 65.4 |
| Organic zinc | | | | | | 21.8 | 21.8 | 43.6 | 65.4 |
| Organic copper | | | | | | 21.8 | 21.8 | 43.6 | 65.4 |
| Total Nitrogen (N) | | | | | | | | | |
| Phosphate (P2O5) | | | | | | | | | |
| Potash (K2O) | | | | | | | | | |
| Chelated Iron | | | | | | | | | |
| Molybenum (Mo) | | | | | | | | | |
| Sprouts (post planting days) | | 3 | 3 | 3 | 3 | 3 | 3 | 3 | 3 |
| Plant Harvest Date | | Aug. 20, 2009 | Aug. 20, 2009 | Aug. 20, 2009 | Aug. 20, 2009 | Aug. 20, 2009 | Aug. 20, 2009 | Aug. 20, 2009 | Aug. 20, 2009 |
| Age at Harvest (days) | | 39 | 39 | 39 | 39 | 39 | 39 | 39 | 39 |
| Weight (gms, as-is) | | 242.59 | 259.33 | 443.38 | 238.55 | 158.66 | 287.23 | 281.26 | 255.05 |
| % of Control | | 100 | 106.90 | 182.77 | 98.33 | 65.40 | 118.40 | 115.94 | 105.14 |
| Soil Analysis (dry weight) | | Submitted | Submitted | Submitted | Submitted | Submitted | Submitted | Submitted | Submitted |
| Moisture (%) | 52.91 | 64.56 | 60.88 | 63.86 | 64.16 | 63.71 | 60.7 | 61.84 | 63.97 |
| pH | 7.1 | 6.9 | 6.9 | 6.9 | 7.1 | 7.2 | 7.1 | 7.2 | 7.3 |
| Aerobic Plate Count (Mcfu/g) | 2.4 | 12.8 | 34 | 25 | 15 | 16 | 36 | 16 | 32 |
| Anaerobic Plate Count (Mcfu/g) | 0.1 | 0.42 | 0.98 | 0.55 | 0.85 | 1.4 | 2 | 0.53 | 1.3 |
| Azotobacter (Mcfu/g) | 3 | 67 | 380 | 240 | 240 | 480 | 260 | 420 | 380 |
| Microbial Activity (ug/10 g soil/day) | 245 | 669 | 681 | 752 | 635 | 1145 | 873 | 1014 | 953 |
| Total Nitrogen (N, %) | 1.13 | 1.44 | 1.23 | 1.58 | 1.26 | 1.13 | 1.3 | 1.42 | 1.39 |
| Ammonia Nitrogen (%) | 0 | nd | 0.01 | 0 | nd | nd | 0.01 | 0.01 | nd |
| Nitrate Nitrogen (%) | nd | nd | nd | nd | nd | nd | nd | nd | nd |
| Organic Nitrogen (%) | 1.06 | 1.44 | 1.22 | 1.57 | 1.26 | 1.13 | 1.29 | 1.41 | 1.39 |
| Phosphorus (P2O5, %) | 0.23 | 0.31 | 0.28 | 0.39 | 0.39 | 0.3 | 0.41 | 0.29 | 0.44 |

TABLE 9-continued

64 Flats, 2 Sq Ft/Flat
Miracle-Gro Garden Soil Composite
Each Flat, 0.25 CUFT soil Soil Analysis

| Flat Number | 1-56 | 57 | 58 | 59 | 60 | 61 | 62 | 63 | 64 |
|---|---|---|---|---|---|---|---|---|---|
| Potassium (K2O, %) | 0.25 | nd | nd | nd | nd | nd | nd | nd | nd |
| Sulfur (S, %) | 0.36 | 0.48 | 0.33 | 0.44 | 0.31 | 0.33 | 0.41 | 0.34 | 0.5 |
| Calcium (Ca, %) | 4.44 | 2.91 | 2.43 | 2.57 | 2.23 | 2.09 | 2.52 | 2.23 | 2.78 |
| Magnesium (Mg, %) | 1.83 | 0.73 | 0.66 | 0.61 | 0.53 | 0.5 | 0.66 | 0.55 | 0.72 |
| Sodium (Na, %) | 0.02 | nd | nd | 0.03 | nd | 0.22 | nd | nd | nd |
| Copper (Cu, ppm) | nd | nd | nd | nd | nd | nd | nd | nd | nd |
| Iron (Fe, ppm) | 7539 | 12960 | 10583 | 11309 | 12162 | 10394 | 12382 | 11593 | 11035 |
| Manganese (Mn, ppm) | 200 | 330 | 258 | 340 | 307 | 278 | 313 | 275 | 275 |
| Zinc (Zn, ppm) | 65.8 | 90.3 | 109.9 | 119 | 86.5 | 68.9 | 96.7 | 83.9 | 88.8 |
| Total salts (per ton) | 3.61 | 1.81 | 1.7 | 1.73 | 1.45 | 1.43 | 1.77 | 1.61 | 1.77 |
| Total Carbon (%) | 25.63 | 21.05 | 21.8 | 25.71 | 18.75 | 18.32 | 21.02 | 22.25 | 22.56 |
| C/N Ratio | 22.8:1 | 14.6:1 | 17.8:1 | 16.3:1 | 14.9:1 | 16.2:1 | 16.2:1 | 15.7:1 | 16.3:1 |
| Chloride | nd | nd | nd | nd | nd | nd | nd | nd | nd |
| Growth Media Extracts | | | | | | | | | |
| pH | 7.5 | | | | | | | | |
| Soluble salts (mS/cm) | 4.1 | | | | | | | | |
| Nitrate nitrogen (mg/L) | 246 | | | | | | | | |
| Phosphorus (P, mg/L) | 0.7 | | | | | | | | |
| Potassium (K, mg/L) | 294 | | | | | | | | |
| Calcium (Ca, mg/L) | 578 | | | | | | | | |
| Magnesium (mg, mg/L) | 210 | | | | | | | | |
| Sodium (Na, mg/L) | 91 | | | | | | | | |
| Plant Cuttings mixed forage (DW basis) | | | | | | | | | |
| Moisture (%) | | 87.22 | 88.88 | 86.93 | 87.6 | 88.61 | 85.95 | 87.1 | 86.36 |
| Dry Matter (%) | | 12.78 | 11.12 | 13.07 | 12.4 | 11.39 | 14.05 | 12.9 | 13.64 |
| Crude Protein (%) | | 16.3 | 23.3 | 14.2 | 21.1 | 26.5 | 23.2 | 19.9 | 23.5 |
| Crude Fat (%) | | 2.14 | 2.3 | 2.38 | 2.85 | 3.04 | 3.69 | 2.55 | 2.89 |
| Acid Detergent Fiber (%) | | 22.3 | 26.5 | 27 | 20.6 | 19.7 | 17.6 | 23.6 | 27.2 |
| Ash (%) | | 14.8 | 15.5 | 12.7 | 14 | 15.3 | 14.3 | 14.3 | 13.5 |
| Total digestible nutrients (%) | | 60.2 | 57.5 | 61.6 | 60.2 | 58.2 | 60.1 | 59.7 | 59.1 |
| Net energy-lactation (Mcal/lb) | | 0.8 | 0.75 | 0.75 | 0.83 | 0.84 | 0.86 | 0.79 | 0.74 |
| Net energy- maint. (Mcal/lb) | | 0.6 | 0.57 | 0.62 | 0.6 | 0.58 | 0.6 | 0.6 | 0.59 |
| Net energy- gain (Mcal/lb) | | 0.32 | 0.34 | 0.35 | 0.32 | 0.34 | 0.32 | 0.36 | 0.35 |
| Digestible Energy (Mcal/lb) | | 1.2 | 1.15 | 1.23 | 1.2 | 1.16 | 1.2 | 1.19 | 1.18 |
| Metabolizable energy (Mcal/lb) | | 1.12 | 1.05 | 1.15 | 1.1 | 1.06 | 1.1 | 1.1 | 1.08 |
| Sulfur (%) | | 0.57 | 0.58 | 0.55 | 0.58 | 0.54 | 0.57 | 0.52 | 0.52 |
| Phosphorus (%) | | 0.31 | 0.36 | 0.29 | 0.33 | 0.36 | 0.38 | 0.31 | 0.36 |
| Potassium (%) | | 4.81 | 5.6 | 4.2 | 4.67 | 5.33 | 4.74 | 4.75 | 4.34 |
| Magnesium (%) | | 0.79 | 0.73 | 0.71 | 0.57 | 0.61 | 0.73 | 0.57 | 0.58 |
| Calcium (%) | | 1.68 | 1.49 | 1.14 | 1.81 | 1.74 | 2.02 | 1.63 | 1.76 |
| Sodium (%) | | 0.07 | 0.09 | 0.05 | 0.11 | 0.07 | 0.06 | 0.07 | 0.06 |
| Iron (ppm) | | 77 | 128 | 93 | 90 | 118 | 167 | 81 | 94 |
| Manganese (ppm) | | 15 | 14 | 12 | 18 | 13 | 14 | 13 | 14 |
| Copper (ppm) | | 4 | 4 | 2 | 4 | 4 | 4 | 4 | 4 |
| Zinc (ppm) | | 74 | 85 | 52 | 106 | 107 | 106 | 95 | 93 |
| Cobalt (ppm) | | 0.52 | 0.45 | 0.17 | 0.47 | 0.39 | 0.36 | 0.3 | 0.28 |

This is the last series of flats. They were planted one day after all the others to test very high mineral levels, such as applied to plants by a product called "Colorburst." Colorburst is an all purpose, dual action (fast acting, long lasting) plant food for promoting "bigger, more beautiful plants." It was utilized because it applied much higher levels of trace minerals—higher than any of the other products that were tested against or considered for the BK 125 product (Cobalt lactate mineral product I or II). Unlike the other mineral products, Colorburst also contains a source of nitrogen, phosphate and potash that supplements the minerals. Minerals include; water soluble copper (copper sulfate), chelated iron (iron EDTA), chelated manganese (manganese EDTA), molybdenum, water soluble zinc (zinc sulfate). The mineral application rates of this product were very high, on a per acre basis (~65K grams/acre).

In this series, the order of magnitude higher mineral application rates were tested, but also wanted to test all of the chelated minerals in combination (zinc, copper, manganese and cobalt) that were produced in pilot batches in the lab. In most of the previous flats the organic chelated cobalt was used in combination with inorganic minerals.

Food Plot Clover Mix seed planted at 5.2 grams/flat was used. Of all the flats, Colorburst in Flat 59 at about 65K grams/acre performed the best. The most important results may be in Flats 62, 63 and 64, where increasing levels of all the chelated minerals used in combination produced growth results ahead of the control. Of further interest here is that as the total levels increased the response lessened, never less than the control, but definitely a trend down with increasing levels of the four (4) chelated materials.

In Flats 62-64 zinc, copper and manganese were used that had been mixed (reacted) together in industry recommended proportions with lactic acid to produce a single product that contained all the mineral lactates together. This solid reaction mass was allowed to partially dissolve in water, then that solution was diluted and applied to the soil in those flats (after having been mixed as well with cobalt lactate powder to yield a mixture of all four mineral lactates). The solution was tested for the level of each mineral lactate and that information is available.

TABLE 10

Effect of cobalt on methane, pH, ammonia-N, and digestibility in continuous cultures of ruminal microorganisms.

| | Treatments | | | | | | | Probability > F | |
|---|---|---|---|---|---|---|---|---|---|
| | Cobalt Carbonate (ppm) | | CoMax New (ppm) | | CoMax Old (ppm) | | | | Source X |
| Item | Control | 0.2 | 1.0 | 0.2 | 1.0 | 1.0 | SE | Source Level | Level |
| Methane, nmol/ml | | | | | | | | | |
| Pre-feeding* | 430.55 | 363.91 | 347.82 | 375.83 | 417.51 | 382.42 | 53.76 | 0.54 0.50 | 0.79 |
| Post-feeding* | 579.30 | 403.14 | 515.35 | 590.46 | 590.74 | 576.21 | 51.13 | 0.04 0.27 | 0.19 |
| Culture pH | | | | | | | | | |
| Pre-feeding* | 5.98 | 5.81 | 5.88 | 5.95 | 5.87 | 5.99 | 0.09 | 0.52 0.38 | 0.63 |
| Post-feeding* | 5.73 | 5.56 | 5.55 | 5.64 | 5.65 | 5.57 | 0.05 | 0.14 0.01 | 0.57 |
| Ammonia-N, mg/dL | 12.23 | 10.79 | 10.88 | 11.80 | 11.95 | 10.32 | 1.49 | 0.57 0.79 | 0.92 |
| NDF Digestibility, % | 23.90 | 23.16 | 17.09 | 20.63 | 27.36 | 15.69 | 2.23 | 0.06 0.42 | 0.001 |
| IVDMTD**, % | 60.52 | 59.35 | 59.17 | 59.50 | 60.67 | 57.94 | 1.16 | 0.42 0.43 | 0.62 |

*Pre-feeding samples taken at 0 hours: Post-feeding values are an average of samples taken at 1, 2, 4 and 6 h after AM feeding
**IVDMTD (in vitro dry matter true digestibility) is based on a 24 h incubation.

Addition of Co as Cobalt Lactate Mineral Complex II had no effect (P>0.10) on methane concentration but providing Co as $CoCo_3$ had a significant negative impact (Table 10). Ammonia-N concentrations were not affected (P>0.10) by dietary treatments. When compared to the control, supplemental Co resulted in a decrease (P<0.01) in culture pH (Table 6). In vitro dry matter true digestibility (IVDMTD) of the control diet did not differ from diets supplemented with Co (Table 10). There was a source x level interaction (P<0.001) for neutral detergent fiber (NDF) digestibility (Table 6). Addition of $CoCo_3$ at the 1.0 ppm had a negative effect on NDF digestibility in contrast to the increase in NDF digestibility observed with Cobalt Lactate Mineral Complex II when added at the 1.0 ppm level. Earlier studies reported no effect on DM and NDF digestibility when Co was added at the 5.0 or 10.0 ppm levels.

TABLE 11

| Sample | ID | Applied Cobalt Weight (gms) | Grass Cuttings Weight (gms, 1st) | Dry Matter Fraction | Grass Dry Weight (gms, 1st) | Cobalt Found (ppm) |
|---|---|---|---|---|---|---|
| 1 | 1CoSo0 | 0 | 19.94 | 0.1597 | 3.184418 | 0.23 |
| 2 | 2CoSo1 | 0.0025 | 31.06 | 0.1525 | 4.73665 | 1.13 |
| 3 | 3CoSo10 | 0.025 | 22.8 | 0.1618 | 3.68904 | 9.92 |
| 4 | 4CoSo100 | 0.25 | 16.33 | 0.1688 | 2.756504 | 39.3 |
| 5 | 5CoSo1000 | 2.5 | 5.15 | 0.1868 | 0.96202 | 75.9 |
| 6 | 6CoAer0 | 0 | 17.28 | 0.1673 | 2.890944 | 0.49 |
| 7 | 7CoAer1 | 7.40E−05 | 15.7 | 0.1703 | 2.67371 | 0.78 |
| 8 | 8CoAer10 | 0.00067 | 17.76 | 0.1685 | 2.99256 | 1.77 |
| 9 | 9CoAer100 | 0.008 | 18.56 | 0.1695 | 3.14592 | 5.18 |

TABLE 11-continued

| Sample | ID | Applied Cobalt Weight (gms) | Grass Cuttings Weight (gms, 1st) | Dry Matter Fraction | Grass Dry Weight (gms, 1st) | Cobalt Found (ppm) |
|---|---|---|---|---|---|---|
| 10 | 10CoAer1000 | 0.069 | 24.03 | 0.1695 | 4.073085 | 44.2 |
| 11 | 11CoXec0 | 0 | 17.41 | 0.1725 | 3.003225 | 0.23 |
| 12 | 12CoXec1 | 6.70E−05 | 24.42 | 0.1694 | 4.136748 | 0.6 |
| 13 | 13CoXec10 | 0.00071 | 23.52 | 0.1662 | 3.909024 | 1.43 |
| 14 | 14CoXec100 | 0.0068 | 12.25 | 0.1808 | 2.2148 | 118 |
| 15 | 15CoXec1000 | 0.084 | 12.97 | 0.1818 | 2.357946 | 154 |

In Table 11, the uptake of cobalt as measured on the grass cuttings that were harvested and submitted for testing. The uptake of cobalt correlated with the application rate and that was mirrored closely at the lower levels.

What is claimed is:

1. A method of stimulating microbes in soil to increase growth in a plant, comprising:
applying a mineral product comprising larch arabinogalactan and particles consisting of cobalt lactate to soil in a lawn, garden, pasture, or field to increase at least one of total aerobic plate count and *Azotobacter* count in the soil.

2. The method of claim 1, wherein the mineral product further comprises a carrier, wherein the carrier is diatomaceous earth, limestone, dextrose, or ground corn cobs.

3. The method of claim 1, wherein the mineral product further comprises one or more metal sulfates.

4. The method of claim 3, wherein the one or more metal sulfates include manganese sulfate, zinc sulfate, and optionally copper sulfate.

5. The method of claim 1, wherein the mineral product further comprises one or more of fiber and enzymes.

6. The method of claim 1, wherein the aqueous solution mineral product further comprises one or more of a scandium lactate compound, a selenium lactate compound, a titanium lactate compound, a chromium lactate compound, an iron lactate compound, and a nickel lactate compound.

7. The method of claim 1, further comprising reducing the particles to a powder.

8. The method of claim 2, wherein the carrier is water.

9. A method of stimulating microbes in soil to increase growth in a plant, comprising:
applying an aqueous solution comprising larch arabinogalactan and particles consisting of cobalt lactate to soil in a lawn, garden, pasture, or field to increase at least one of total aerobic plate count and *Azotobacter* count in the soil.

10. The method of claim 9, wherein the aqueous solution further comprises manganese sulfate, zinc sulfate, and optionally copper sulfate.

11. The method of claim 9, wherein the aqueous solution further comprises one or more of fiber and enzymes.

12. The method of claim 10, wherein the aqueous solution comprises about 2% to about 10% of the one or more metal sulfates by weight.

13. The method of claim 11, wherein the aqueous solution comprises about 1% to about 5% of fiber by weight and at least 2.1% of *yucca* by weight.

14. The method of claim 11, wherein the aqueous solution comprises about 0.1% to about 2% of enzymes by weight.

15. The method of claim 9, wherein the mineral product further comprises about 2.1% to about 5% of *yucca* by weight.

16. A method of stimulating microbes in soil to increase growth in a plant, comprising:
applying a mineral product comprising larch arabinogalactan, a powder consisting of cobalt lactate, and at least one of zinc lactate, copper lactate, and manganese lactate to soil in a lawn, garden, pasture, or field to increase at least one of total aerobic plate count and *Azotobacter* count in the soil.

17. The method of claim 16, wherein the mineral product further comprises one or more metal sulfates.

18. The method of claim 16, wherein the mineral compound further comprises one or more of manganese sulfate, zinc sulfate, and copper sulfate.

* * * * *